(12) United States Patent
Phillips

(10) Patent No.: US 7,655,049 B2
(45) Date of Patent: Feb. 2, 2010

(54) SOCKET INSERT HAVING A BLADDER SYSTEM

(76) Inventor: Van L. Phillips, 33000 Navarro Ridge Rd., Albion, CA (US) 95410

( * ) Notice: Subject to any disclaimer, the term of this patent is extended or adjusted under 35 U.S.C. 154(b) by 0 days.

(21) Appl. No.: 10/359,514

(22) Filed: Feb. 5, 2003

(65) Prior Publication Data

US 2003/0181990 A1 Sep. 25, 2003

Related U.S. Application Data

(63) Continuation-in-part of application No. 10/207,230, filed on Jul. 26, 2002, now abandoned.

(60) Provisional application No. 60/308,061, filed on Jul. 26, 2001.

(51) Int. Cl.
*A61F 2/80* (2006.01)

(52) U.S. Cl. .......................................................... 623/37

(58) Field of Classification Search ............. 623/33–37, 623/26, 56; 297/199, 200; 36/153
See application file for complete search history.

(56) References Cited

U.S. PATENT DOCUMENTS

| 980,457 | A | 1/1911 | Toles |
|---|---|---|---|
| 1,117,725 | A | 11/1914 | Tullis |
| 1,586,015 | A | 5/1926 | Underwood |
| 2,464,443 | A | 3/1949 | Ganoe et al. |
| 2,634,424 | A | 4/1953 | O'Gorman |
| 3,889,301 | A | 6/1975 | Bonner, Sr. |
| 4,655,779 | A | 4/1987 | Janowiak |
| 4,892,554 | A | 1/1990 | Robinson |
| 4,911,724 | A | 3/1990 | Fikes |
| 4,923,475 | A | 5/1990 | Gosthnian et al. |

(Continued)

FOREIGN PATENT DOCUMENTS

DE 94 19 211.1 2/1995

(Continued)

OTHER PUBLICATIONS

Michael Love Associates, Inc., Amputee Treatment Center. Pump It Up! Prosthetic Socket. http://www.amputee-center.com/pumpitup.htm. Accessed Apr. 25, 2002.

(Continued)

*Primary Examiner*—Corrine McDermott
*Assistant Examiner*—Cheryl Miller
(74) *Attorney, Agent, or Firm*—J. Mark Holland & Associates

(57) ABSTRACT

A prosthetic device having a socket with an insert having a bladder system for monitoring and compensating for volume fluctuations in a residual limb is provided. A plurality of bladders are preferably provided, in one embodiment, substantially only on a posterior portion of the socket. The bladders may be organized into zones, with the zones being inflatable to differing pressures depending on volume fluctuations in a residual limb. Pressure sensors may be provided for each bladder or for each zone, and flow regulators may be provided to control fluid flow into or out of the bladders or zones of bladders based on readings from the pressure sensors to control volume within the insert. Alternatively, bladders can be manually inflated depending on an amputee's needs.

63 Claims, 26 Drawing Sheets

U.S. PATENT DOCUMENTS

| | | | |
|---|---|---|---|
| 5,108,456 A | | 4/1992 | Coonan, III |
| 5,133,776 A | * | 7/1992 | Crowder .................... 623/37 |
| 5,156,629 A | | 10/1992 | Shane et al. |
| 5,158,570 A | | 10/1992 | Schey et al. |
| 5,246,464 A | | 9/1993 | Sabolich |
| 5,258,038 A | | 11/1993 | Robinson et al. |
| 5,290,319 A | | 3/1994 | Phillips |
| 5,314,497 A | | 5/1994 | Fay et al. |
| 5,376,132 A | | 12/1994 | Caspers |
| 5,387,245 A | | 2/1995 | Fay et al. |
| 5,405,405 A | | 4/1995 | Love |
| 5,405,409 A | | 4/1995 | Knoth |
| 5,443,525 A | | 8/1995 | Laghi |
| 5,443,529 A | | 8/1995 | Phillips |
| 5,464,443 A | | 11/1995 | Wilson et al. |
| 5,503,543 A | | 4/1996 | Laghi |
| 5,507,834 A | | 4/1996 | Laghi |
| 5,507,837 A | | 4/1996 | Laghi |
| 5,534,034 A | | 7/1996 | Caspers |
| 5,549,709 A | | 8/1996 | Caspers |
| 5,593,456 A | | 1/1997 | Merlette |
| 5,728,168 A | | 3/1998 | Laghi et al. |
| 5,735,909 A | | 4/1998 | Caspers |
| 5,746,772 A | | 5/1998 | Jacobs |
| 5,784,807 A | * | 7/1998 | Pagel ........................... 36/93 |
| 5,813,142 A | | 9/1998 | Demon |
| 5,888,230 A | | 3/1999 | Helmy |
| 5,888,231 A | | 3/1999 | Sandvig et al. |
| 5,897,517 A | | 4/1999 | Laghi |
| 5,904,722 A | | 5/1999 | Caspers |
| 5,916,664 A | * | 6/1999 | Rudy ......................... 428/178 |
| 5,944,760 A | | 8/1999 | Christensen |
| 6,120,530 A | * | 9/2000 | Nuckols et al. ............ 607/108 |
| 6,120,547 A | | 9/2000 | Christensen |
| 6,149,691 A | | 11/2000 | Fay et al. |
| 6,161,240 A | * | 12/2000 | Huang ........................... 5/710 |
| 6,197,068 B1 | | 3/2001 | Christensen |
| 6,231,616 B1 | | 5/2001 | Helmy |
| 6,231,617 B1 | | 5/2001 | Fay |
| 6,241,776 B1 | | 6/2001 | Christensen |
| 6,368,357 B1 | * | 4/2002 | Schon et al. ................. 623/37 |
| 6,406,499 B1 | | 6/2002 | Kania |
| 6,409,691 B1 | * | 6/2002 | Dakin et al. .................... 602/5 |
| 6,423,098 B1 | | 7/2002 | Biedermann |
| 6,436,149 B1 | | 8/2002 | Rincoe |
| 6,440,173 B1 | | 8/2002 | Meyer |
| 6,454,812 B1 | | 9/2002 | Laghi |
| 6,585,774 B2 | * | 7/2003 | Dean et al. .................... 623/37 |
| 6,892,477 B2 | * | 5/2005 | Potter et al. ..................... 36/29 |
| 7,181,867 B2 | * | 2/2007 | Litchfield et al. ............... 36/29 |
| 2001/0005798 A1 | | 6/2001 | Caspers |
| 2001/0016781 A1 | | 8/2001 | Caspers |
| 2001/0045540 A1 | | 11/2001 | Iyengar |
| 2002/0040248 A1 | | 4/2002 | Karason |
| 2002/0091449 A1 | | 7/2002 | Caspers et al. |
| 2002/0095220 A1 | | 7/2002 | Slemker et al. |
| 2002/0099450 A1 | | 7/2002 | Dean, Jr. et al. |
| 2002/0103545 A1 | | 8/2002 | Arbogast et al. |
| 2002/0116071 A1 | | 8/2002 | Slemker et al. |
| 2002/0116072 A1 | | 8/2002 | Rubie et al. |
| 2002/0128727 A1 | | 9/2002 | Merlette et al. |
| 2002/0133237 A1 | | 9/2002 | Christesen |

FOREIGN PATENT DOCUMENTS

| | | |
|---|---|---|
| DE | 43 25 445 A1 | 6/1995 |
| EP | 1 127 541 A1 | 8/2001 |
| GB | 2 124 493 A | 2/1984 |
| WO | WO 94/05177 | 3/1994 |
| WO | WO 95/03760 | 2/1995 |
| WO | WO 00/03665 | 1/2000 |
| WO | WO 00/23016 | 4/2000 |
| WO | WO 00/27317 | 5/2000 |
| WO | WO 00/74611 A2 | 12/2000 |
| WO | WO 01/54631 A1 | 8/2001 |
| WO | WO 02/02034 A1 | 1/2002 |
| WO | WO 02/28326 A1 | 4/2002 |
| WO | WO 02/067825 A2 | 9/2002 |

OTHER PUBLICATIONS

Silicone Liners Suspension. http://www.oandp.com/products/silicone_liners_suspension.asp. Accessed Apr. 24, 2002.

Sandia National Laboratories. http://www.sandia.gov/media/NewsRel/NR2000/smartleg.htm. Accessed Apr. 24, 2002.

TEC Interface Systems. Http://tecinterface.com. Accessed Apr. 24, 2002.

* cited by examiner

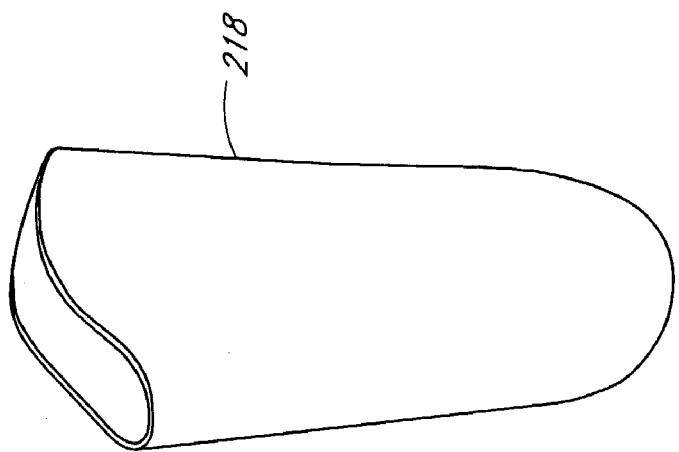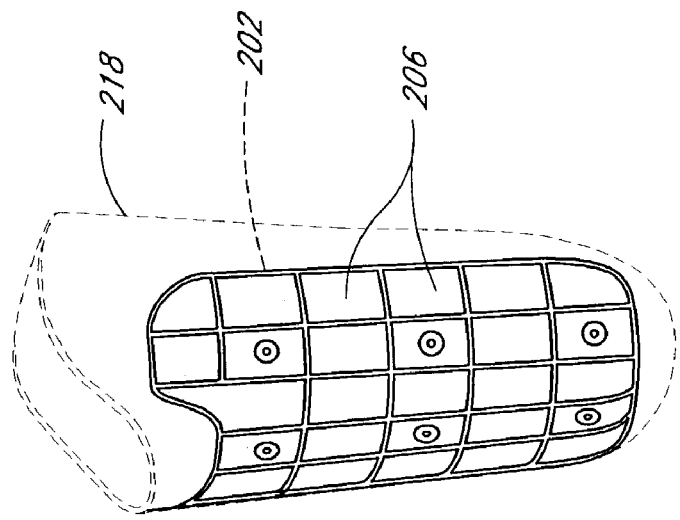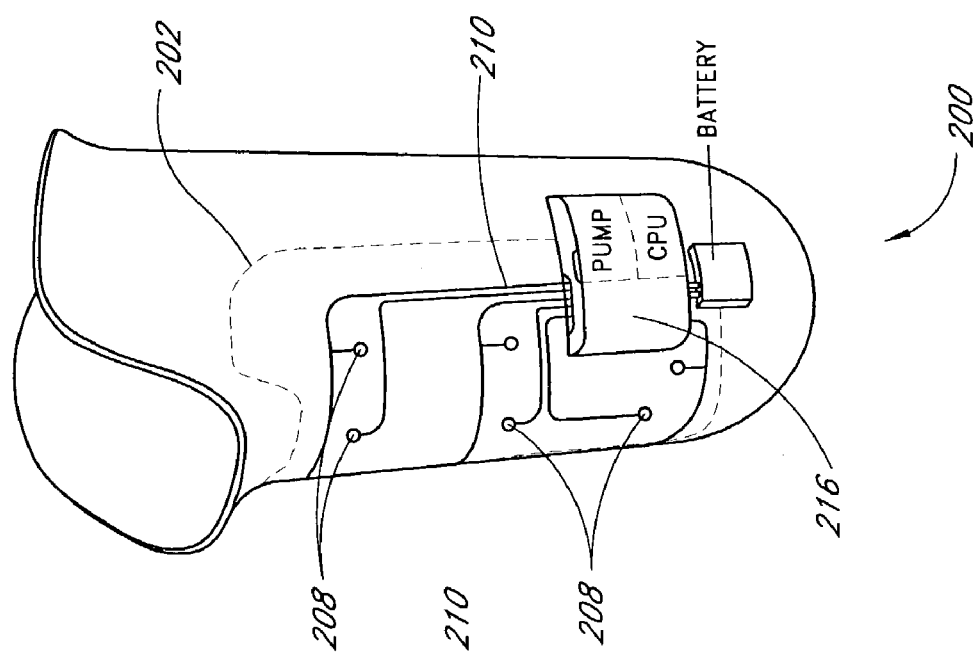

SOCKET INSERT HAVING A BLADDER SYSTEM

CROSS-REFERENCE TO RELATED APPLICATIONS

This application is a continuation-in-part of U.S. Application Ser. No. 10/207,230, filed Jul. 26, 2002 now abandoned, which claims priority to U.S. Provisional Application Ser. No. 60/308,061, filed Jul. 26, 2001. Both of these applications are hereby incorporated by reference in their entireties.

BACKGROUND OF THE INVENTION

1. Field of the Invention

The present invention relates to prosthetic devices, and in one embodiment, relates to an insert for the socket of a prosthetic device incorporating multiple cells to compensate for volume fluctuations of a residual limb.

2. Description of the Related Art

With the ever-increasing number of amputees needing prosthetic devices, various types of prosthetic devices have been developed. In the past, prosthetic devices usually comprised some form of artificial limb or rod. More recently, other devices have been made to imitate the structure of the human limbs, as well as to simulate their natural movement. Many consisted of a hinge to allow movement at joints. These devices also include a socket for connecting the prosthetic device to the residual limb.

Most new amputations are either slightly bulbous or cylindrical in shape while older amputations that may have had a lot of atrophy are generally more conical in shape. Residual limbs may further be characterized by their various individual problems and configurations including the volume and shape of a residual limb and possible scar, skin graft, bony prominence, uneven limb volume, neuroma, pain, edema, or soft tissue configurations.

The volume of a residual limb changes significantly over the course of a day and throughout an amputee's lifetime. Consequently, sockets for receiving a residual limb may not always fit properly due to this volume variation. Moreover, particular activities may cause changes to the volume within a socket. The situation is analogous to how a ring worn on a finger may sometimes feel loose or tight at various times during the day.

Prior art attempts to compensate for this volume variation have included the use of silicone liners and inflatable bladders. Such devices however do not adequately address specific volume variations for an amputee's residual limb within a socket.

Attempts have also been made to improve the comfort of the socket by utilizing air cushions in various prosthetic devices, but none were designed to enhance activity levels beyond the expected sedentary levels of most amputees or compensate for volume fluctuations. Suction suspension sockets, wherein an elevated vacuum is provided between the liner and the socket wall, have also been designed to try to compensate for the volume fluctuations. A drawback to suction suspension arises from the fact that a standard socket, whether flexible or rigid, has a fixed, constant volume.

Another problem with air cushions is that such devices apply constant, unrelieved pressure. The situation is similar to that of bed sores, where the constant pressure can adversely affect blood supply. Moreover, because air is compressible, air cushions are too bouncy, which can cause portions of a residual limb to simply bounce off of the cushion, rather than providing effective volume control.

Some individuals fit socks over their residual limb in an attempt to make the prosthesis more comfortable. Several layers of socks may form a reasonably soft cushion, but socks are not able to protect a particular point or area where extra support or volume is needed. The socks provide the same amount of support everywhere. Moreover, most residual limbs shrink in size as the day progresses because walking and other activities drive blood and other fluid out of the residual limb, resulting in the need for additional layers of socks during the day. It is cumbersome to remove the socket, add or remove additional pairs of socks, and reattach the socket several times per day.

Thus, there is a need for an improved system that compensates for the volume fluctuations of the residual limb for improved performance and comfort of the prosthetic device.

SUMMARY OF THE INVENTION

The preferred embodiments of the present invention represent a substantial improvement over the prior art prosthetic devices in that the preferred embodiments provide for an insert having a bladder system to be inserted into the socket which compensates for the volume fluctuations of the residual limb. Monitoring of such volume fluctuations can be done either automatically or manually by the amputee. The socket insert in one embodiment is substantially adjustable, such that unique characteristics of each amputee, such as changes in volume, weight and changes in weight, size and gait, as well as particular needs, can be accommodated.

It has been discovered that the volume fluctuations primarily occur at the posterior portion of the residual limb. This is due at least in part because the posterior portion of a limb is mostly muscle and tissue, whereas the anterior portion of a limb is primarily bone. Accordingly, in a preferred embodiment, the bladder system is provided only at the posterior portion of the socket, accommodating for these large volume fluctuations. Moreover, the bladder system preferably allows for migration of fluid to bladders where more or less pressure is desired, depending on the particular muscles being supported or due to changes in volume due to the amputee's activity, movement of the residual limb, etc. It is also envisioned that the bladder system may extend around the entire socket. The insert is also preferably interchangeable or removable.

The bladder system is preferably made of a plurality of interconnected fluid-filled cells, which may be organized into zones. The bladder system accommodates for the volume fluctuations by adjusting the volume of fluid within each cell or, alternatively, within each zone. The entire insert may contain a consistent volume of fluid. Alternatively, a reservoir and pump system may be provided for adjusting the volume of fluid within the insert, zones, and/or cells. The division of the bladder system into multiple zones or cells allows for individual control over volume in specific desired locations around the socket.

In accordance with one preferred embodiment, a prosthetic device is provided comprising a socket defining an interior cavity having an anterior portion and a posterior portion for receiving a residual limb. A plurality of bladders is disposed within the interior cavity substantially only on the posterior portion. The bladders are adapted to receive a fluid medium and are organized into a plurality of zones. Each of the zones includes at least one bladder. Fluid flow into and out of the zones is controllable such that different zones can be filled with fluid to differing pressures. This provides volume control over the bladders in specific desired locations to accommodate volume fluctuations at specific locations of the residual limb when inserted into said interior cavity.

In accordance with another preferred embodiment, a prosthetic device comprising a socket and a plurality of bladders disposed on an interior surface of the socket is provided. The bladders are organized into a plurality of zones, such that each of the zones includes at least one bladder and each of the bladders within a zone are in fluid communication with the other bladders within the zone. A plurality of pressure sensors is also provided, such that each zone includes at least one pressure sensor. The bladders may also include a plurality of flow regulators, wherein at least one flow regulator regulates flow into a bladder within each zone.

In one embodiment, a method of fitting a residual limb to a socket for a prosthetic device is provided. The method includes providing a prosthetic device having a socket and a plurality of inflatable bladders provided therein. Each of the bladders are preferably grouped into individual zones. The pressure of the bladders in each of the zones is monitored and may be adjusted based on the monitoring of the pressure of the bladders, by transferring fluid into and out of the bladders.

In another embodiment, a socket insert for insertion into a socket receiving a residual limb is provided. The socket insert comprises a plurality of bladders being adapted to receive a fluid medium. Fluid flow into and out of said zones is controllable such that different zones can be filled with fluid to differing pressures. In one embodiment, the bladders are organized into at least four zones, each of the zones including at least four interconnected bladders. The socket insert as described above may be positioned on the interior surface of a socket, more preferably only partially circumferentially around the interior surface of the socket.

In another embodiment, a prosthetic device is provided comprising a socket for receiving a residual limb, the socket having an interior surface. A plurality of bladders adapted to receive a fluid medium is positioned at least partially on the interior surface. The bladders are organized into a plurality of zones, each of the zones including a plurality of bladders and each of the bladders within a zone being in fluid communication with the other bladders within the zone. Fluid flow into and out of the zones is controllable such that different zones can be filled with fluid to differing pressures.

In another embodiment, the prosthetic device comprises a plurality of bladders sized and configured to be positioned adjacent an interior surface of a socket. At least some of the bladders contain an incompressible fluid. Each of the bladders has a maximum dimension of about 2 inches or less. At least some of the bladders are interconnected such that fluid can flow from one bladder to another. In one embodiment, a socket is provided receiving the plurality of bladders, and the plurality of bladders may be provided on a socket insert secured to the interior surface of the socket.

The bladder system of one preferred embodiment is also substantially lightweight, which is desirable when considering that the prosthesis is attached to the end of an amputee's residual limb. The lighter the prosthetic device, the easier it is for the amputee to secure the prosthetic device to the residual limb. A lightweight prosthesis is also easier to control, which is significant if the amputee is to participate in activities such as tennis and jogging.

The preferred embodiments also enable the amputee to manually adjust the volume of the bladders. In one embodiment, each bladder can be adjusted independently, such that an almost infinite variety of performance levels can be obtained. This adjustability feature is significant when considering the infinite number of characteristics of individual amputees that must be accommodated by a prosthetic device.

The preferred embodiments can accommodate amputees who are light, heavy, sedate, rigorously active, young, old, small, large, or have particular and specific needs.

One of ordinary skill in the art can readily see that any configuration and shape can be utilized to provide specific advantages.

The multiple bladder system of the preferred embodiments allows the amputee to maintain the pressure of the bladders relatively low. In previous bladder devices, one had to pump a single bladder to substantially high pressure to avoid migration of air. However, a bladder at such high pressure may be too stiff for some amputees, and can cause atrophy. Moreover, a bladder under high pressure is more prone to leakage and rupture than multiple bladders at lower pressures. Multiple bladders also desirably offer additional volume control for specific locations within a socket.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIGS. 2A-C are perspective views showing a socket, bladder system and liner having preferred features.

DETAILED DESCRIPTION OF THE PREFERRED EMBODIMENTS

Figure 1:
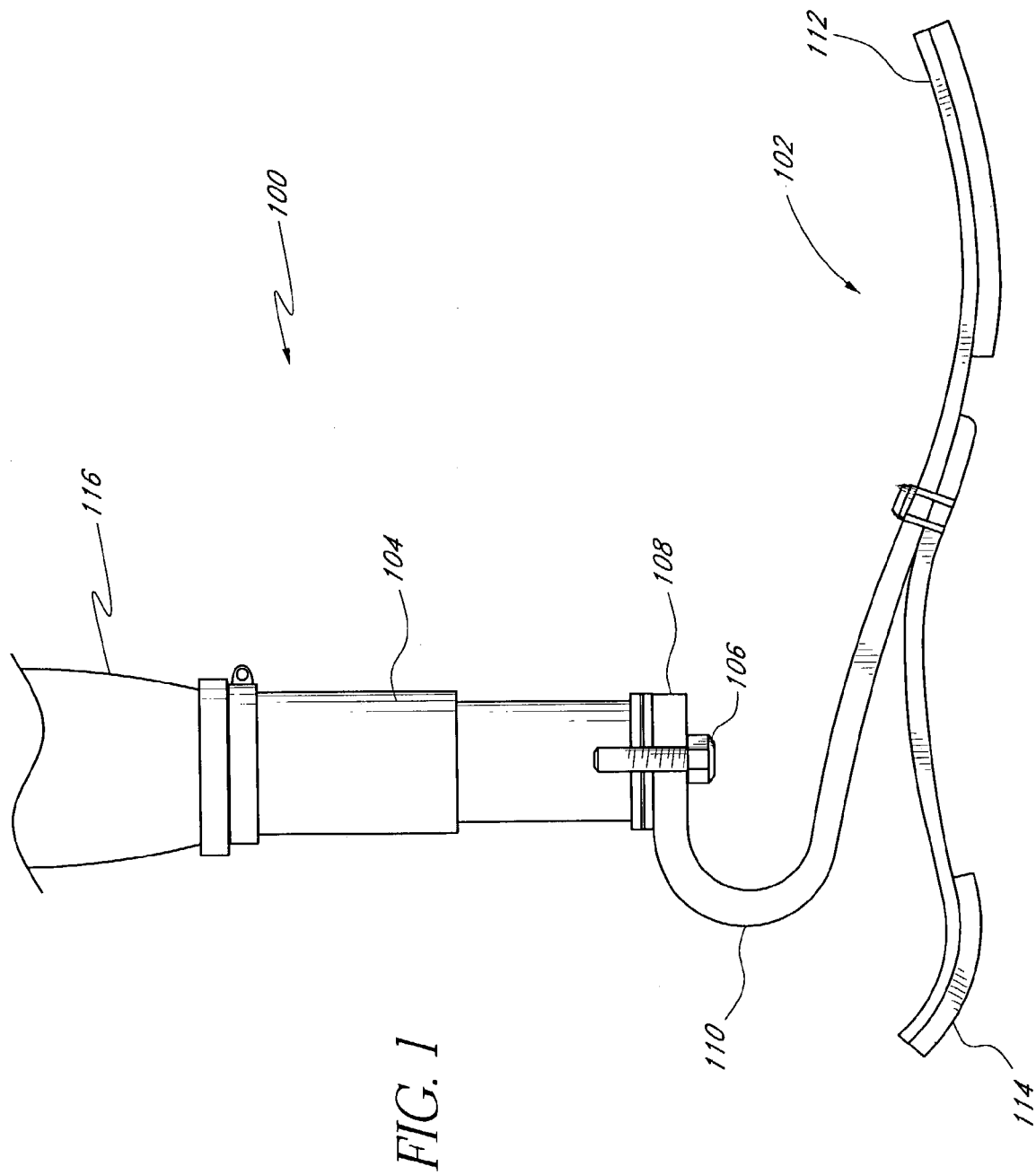
FIG. 1 is a perspective view which shows a prosthetic device having a socket with an inflatable bladder system.

Fluctuations in the size of the residual limb present a continuing problem for amputees. As used herein, residual limb encompasses both above-the-knee and below-the-knee amputees, but it will be appreciated that certain embodiments of the invention may have applicability to other amputated locations of the body. Such fluctuations result from several causes, including swelling and reduction in swelling from recent surgical wounds and occasional systemic fluid shifts due to amputee activities which affect even the well-healed residual limb. If the fluid in the limb increases, the socket may become too small or may not fit properly, creating undue friction and pressure. If the fluid in the limb decreases, the socket may become too large and the gripping effect sought to be achieved by the contoured design of the socket is reduced. The pockets of trapped air between the reduced limb and the socket may also produce noises or flatulations.

A particular problem arises with the contoured design of sockets. For example, where the interior of a socket is at least partially contoured, for example in its anterior portion, the stump should desirably be positioned against the contour for an ideal fit. However, if the fluid in the limb decreases, the stump can slip, rotate or otherwise move away from the contour, causing pressure against the stump in locations where the stump is not correctly pressed against the contour. Thus, as described in preferred embodiments below, desired pressure placed on the posterior side of the stump can ensure that the stump is placed correctly against the anterior wall of the socket.

One embodiment of the present invention includes a system of inflatable compartments, which permit temporary adjustments to accommodate changes in the volume or size of the residual limb. Moreover, the inflatable compartments provide an improved gripping effect which stabilizes the residual limb in the socket against vertical displacement and unwanted rotation within the socket. Thus, the fit of the prosthesis can be maintained without the cost or inconvenience of modifying or replacing the socket.

As used herein, the term 'socket' is a broad term and is used in its ordinary meaning and includes, without limitation, a device for receiving a residual limb of an amputee and adapted for use with a prosthetic limb.

As used herein, the term 'bladder system' is a broad term and is used in its ordinary meaning and includes, without limitation, a plurality of small interconnected bladders or cells.

As used herein, the term 'cell' is a broad term and is used in its ordinary meaning and includes, without limitation, a fluid-filled pouch or bladder.

As used herein, the term 'liner' or 'socket liner' is a broad term and is used in its ordinary meaning and includes, without limitation, a liner adapted to receive an amputee's residual limb, the liner separating the limb from the socket which receives the residual limb.

As used herein, the term 'insert' or 'socket insert' is a broad term and is used in its ordinary meaning and includes, without limitation, a device adapted to be used with a socket, which may be interchangeable, removable, or permanent. The insert can be integrally formed with the socket. Moreover, the insert can be provided either on an interior or exterior surface of a separate socket liner. The insert can also be embedded within or simply be part of the socket liner itself, such that the insert and the liner are essentially one piece.

With reference to FIG. 1, the prosthesis of one embodiment comprises a prosthetic device with an adjustable bladder system. The prosthetic device structure can be, but is not limited to, any of the various prosthetic devices disclosed in my previous patents and pending applications, including U.S. Pat. Nos. 4,822,363, 5,037,444 and 5,181,932, the entirety of each of which is hereby incorporated by reference, or any other prosthetic device. It should be understood that the preferred embodiments illustrated herein as a prosthetic device to be worn as an artificial leg by a below the knee amputee, has equal application to other types of artificial limbs, such as above the knee prosthetics and similar or like prosthetic devices. Alternatively, a foot prosthesis device having a slightly different structure can also be utilized.

As shown in FIG. 1, the prosthetic device structure 100 comprises a curvilinear foot portion 102 extending downward from a pylon member 104 which extends from the residual limb of the amputee. The foot portion 102 is secured to the pylon member 104 by at least one bolt 106, which extends through the upper extremity 108 of the foot portion 102, and through an attachment connector which conforms to the outer surface of the pylon. The foot portion 102 extends downward and forward therefrom, bending about an ankle section 110. The foot portion 102 also extends from the ankle sections 110 forward to a toe end 112 of the prosthesis 100. Also, attached to the underside of the foot portion 102 is a heel portion 114 extending rearward therefrom. In a preferred embodiment, the foot portion 102 is an integral member formed from superimposed laminates utilizing a resin impregnated high-strength filament structure, as disclosed in my previous U.S. Pat. No. 4,547,913, the entirety of which is incorporated herein by reference, and my previous U.S. Pat. Nos. 4,822, 363 and 5,037,444.

A socket 116 is provided where the prosthetic device is connected to the residual limb of the amputee. Inflatable compartments comprising a bladder system preferably line the interior of the socket, as described below. The system preferably accommodates volume fluctuations in at least the posterior portion of the socket, top to bottom, ensuring correct and even counter support anteriorly. The prosthetic device may also include a system for controlling and adjusting the pressure within the bladder system either manually or automatically. A fluid communication system may also be provided, connecting the individual bladders or cells to one another. At least one reservoir and at least one valve may also be provided in conjunction with fluid communication system. The bladder system may be passive, active or semi-active, depending on the particular needs of each amputee. Further details of this system are described below.

Figure 3:
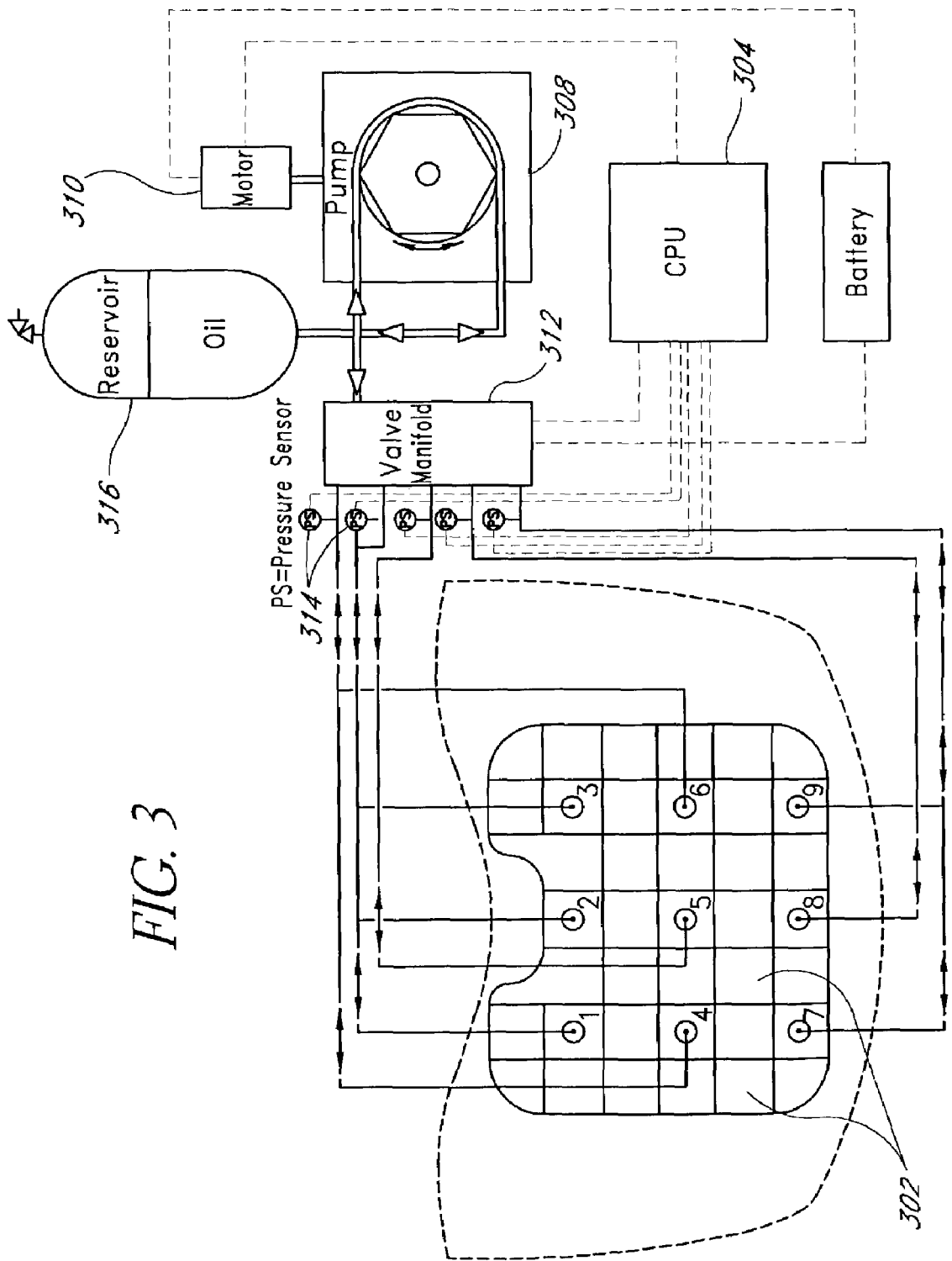
FIG. 3 is a schematic diagram showing a control system for use with the inflatable bladder system of FIGS. 2A-C.

An overview of a socket bladder system is shown in FIGS. 2A-3. FIG. 2A illustrates a socket 200 having an array of fluid-carrying tubes 210 adapted to provide fluid from a control system 216 to fluid supply valves 208. These fluid supply valves 208 preferably communicate with an array of fluid-containing bladders or cells 206, provided on a socket insert 202, shown in FIG. 2B. The fluid-carrying tubes 208 can be provided on the exterior of the socket, on the interior of the socket, or even within the walls of the socket. When on the outside or inside of the socket, the fluid carrying tubes may be covered by a protective sleeve to guard them from damage. Modular quick connect elbow fittings can be provided extending through the socket wall in order to allow easy replacement of the cell array insert. Similarly, the control system 216, as described below, can also be provided either on the exterior, interior or within the socket itself. The socket insert 202 is preferably provided in an internal recess within the socket 200, and in one embodiment as illustrated, is adapted to cover a posterior half of the user's leg. FIG. 2C shows a liner 218 which will preferably be disposed such that it encloses the socket insert 202 within the socket and the residual limb is not in contact with the socket insert.

The socket insert 202 is preferably secured to the interior wall of the socket. This prevents any shifting of the bladder system. The interior surface of the insert is preferably relatively soft and flexible and, thus, the insert will move inwardly to grip the residual limb when one or more of the cells are inflated, and/or to apply desired pressure against the residual limb to ensure desired positioning of the limb within the contour of the socket. The socket wall, however, is preferably somewhat stiff, preventing movement between the insert and the residual limb. The socket insert 202 may be secured to the socket by a bonding agent such as glue, or with bands of elastic material, which are flexible, yet retain the cells relatively securely against the socket. It is noted, however, that the cells can be secured to the prosthesis by a number of different methods, and should not be limited to those discussed herein. In one alternate embodiment, the insert or bladder system can be an integral part of the socket wall. In another alternate embodiment, the insert or bladder system can be provided on the liner 218, either attached or secured to one of its surfaces or embedded temporarily or permanently therein.

In a preferred embodiment, the socket insert 202 may be removable so that the amputee may use the prosthesis without the cells. Moreover, the socket may be used even when the cells are deflated or contain no fluid. This is significant because, in some situations the cells may become damaged or punctured. By permitting the amputee to continue to use the prosthesis, the amputee's activities are not entirely limited.

As illustrated, the cells 206 of the socket insert 202 form a fluid communication system to provide volume control over at least the posterior portion of the socket. The cells 206 are preferably arranged into a plurality of zones, wherein an individual fluid supply valve 208 connects the control system 216 with a bladder within each zone. These zones may or may not be interconnected, as described below. Alternatively, as described below, fluid supply valves can be provided for every bladder of the socket insert, or a central valve can be used to supply fluid into all of the bladders.

The design of the cells in the bladder system is dependent on the needs of the amputee. Preferred cell embodiments are described below. Preferably, the insert is removable and interchangeable, such that standardized inserts having various bladder arrangements may be substituted for various activities or changes in shape, size, or weight. Alternatively, the insert may be a custom fabrication procedure, such that the needs of each individual amputee may be met. Inserts or bladders may be customizable in a modular fashion, such that a user can assemble different zones of cells in a desired configuration. In this manner, the layout of the cells, the number of cells, or the size of the cells is adjustable.

Control System

The control system 216 is preferably provided on the exterior of the socket 200, and controls the fluid supply to the bladders or cells 206. Preferably, the control system includes a pump for pumping fluid to individual cells, preferably from a fluid reservoir described with respect to FIG. 3. FIG. 3 illustrates schematically one embodiment of a control system to control fluid flow in individual cells of a cell array 302. As illustrated in FIG. 3, the cell array comprises nine zones, each of the zones having a plurality of interconnected bladders, as described below. Pressure sensors 314 are preferably associated with each of the zones. As illustrated, in one embodiment a single pressure sensor can be used to control the volume of fluid in multiple zones. Alternatively, there may also be a single pressure sensor for every zone, or even a single pressure sensor for every bladder. A valve manifold 312 directs fluid into or out of the zones depending on readings from the pressure sensors, as determined by CPU 304. A fluid reservoir 316 supplies fluid to the valve manifold, using a motor 310 and a pump 308. In the embodiment shown, the fluid is oil, although other fluids as described below may also be used. The fluid reservoir 316 can also be used to store fluid exiting the inflatable cells when pressure in those cells is desired to be reduced. A battery 306 is provided to power the system.

In one preferred embodiment, the control system uses pressure sensors 314 to compare the pressure in individual bladders or a zone of bladders with a predetermined calculated threshold pressure. The pressure sensor relays the pressure data to the CPU 304. The CPU 304, based on the data received from monitoring the pressure, controls the pump 308 and/or valve manifold 312, such that additional fluid is provided to cells or zones having decreased pressure, while fluid is removed from cells or zones having increased pressure, thereby accommodating for fluctuations in volume of a residual limb. If a threshold pressure is exceeded, a CPU opens a valve controlling the exit of fluid from a fluid cell or zone of cells disposed in the socket to allow fluid to escape and thereby reduce the volume of the cell or zone of cells. Alternatively, if the pressure within a cell or zone of cells is too low, a valve can be opened directing fluid into the cell or zone of cells.

The bladder system may be constructed with pressure sensing devices built into the cells, adjacent to the cells, or the pressure sensors may be located at a point along a supply line for each cell. The pressure sensor in one embodiment is a pressure sensitive variable capacitor, which may be formed by a pair of parallel flexible conductive plates disposed on each side of a compressible dielectric. The dielectric may be made from any suitable material such as rubber or other suitable elastomers. The outside of the flexible conductive plates may be covered by a flexible sheath to protect the outside of the conductive plates. Other pressure sensing devices include pressure sensitive variable resistors, pressure transducers, piezoelectric transducers or any other known pressure sensing device may also be used. The pressure sensing system also preferably includes pressure sensing circuitry, which converts the change in pressure detected by the pressure sensing device into digital data.

The valves of the fluid communication system may be of any type, and it will be appreciated that the term "valve" is a broad term and is used in its ordinary meaning and includes, without limitation, solenoid, ball, gate, check, butterfly, globe, needle, pop-safety, relief, regulating, control, float, mixing, switching, actuator, lockout, and multi-port valves. As described further below, each cell may have its own valve, each zone may have its own valve, and/or a central valve may be provided for the entire system. The system may also be constructed with valves built into the duct system interconnecting adjacent bladders, as described below.

Auxiliary reservoirs may be also be provided for the insert. In addition, reservoirs may be provided for each zone of cells to maintain pressure within the bladder system.

Figure 22:
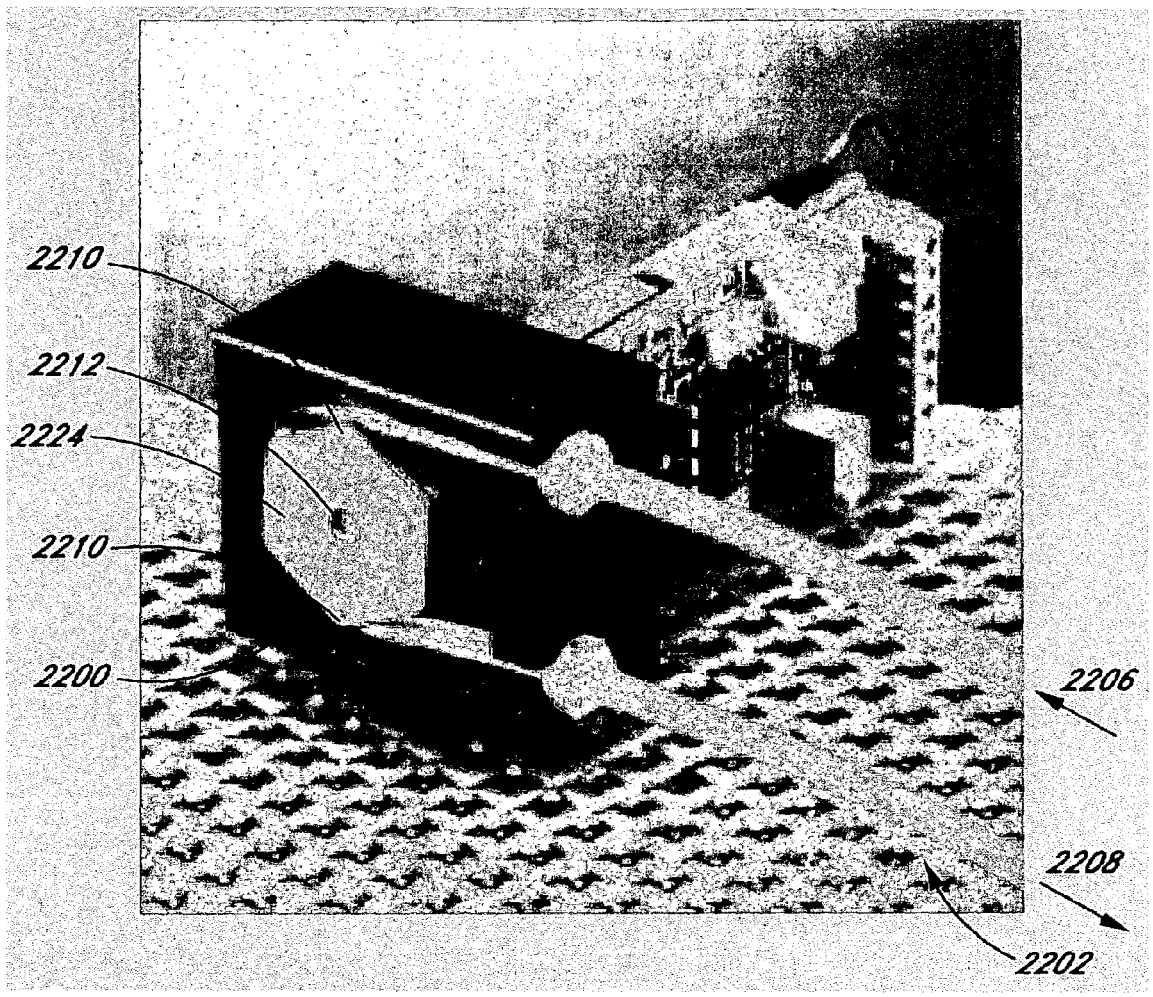
FIG. 22 is a perspective view of a peristaltic pump having preferred features and advantages.

The pump 308 used to inflate and deflate the cells may preferably be located within a wall of a socket. Alternatively, a central pump may be provided outside of the socket. One embodiment of a suitable pump is shown in FIG. 22 and described below. In an alternative embodiment, the fluid may be moved toward or away from the cell array by using a compressed gas such as carbon dioxide to selectively compress a portion of tubing or a flexible diaphragm in order to move the fluid in a desired direction.

The control system preferably includes a programmable microcomputer having conventional RAM and ROM or CPU 304. The CPU 304 receives information from the pressure sensing system indicative of the relative pressure sensed by each pressure sensing device. The control system receives digital data from the pressure sensing circuitry proportional to the relative pressure sensed by the pressure sensing devices. The control system is also in communication with the fluid valves to vary the opening of the fluid valves and thus control the fluid flow. In one embodiment, where solenoid valves are used, the control system is in electrical communication with the fluid valves.

In a preferred embodiment, the control system begins by performing an initialization process which is used to set up pressure thresholds for each zone. During initialization, the fluid valves are fully closed, and no fluid can escape the fluid cells regardless of the amount of pressure applied to the fluid cells. As the user begins to move, the control system receives and stores measurements of the change in pressure of each zone from the pressure sensing system.

The control system then computes an upper and lower threshold pressure for each cell or zone based on the measured pressure for a given number of strides. The calculated upper threshold pressure, in this embodiment, will be less than the average peak pressure measured. Alternatively, these thresholds can be predetermined or entered by the user or prosthetist.

The control system will continue to monitor data from the pressure sensing system and compare the pressure data from each zone with the lower and upper pressure thresholds of that zone. When the control system detects a measured pressure that is greater than the upper pressure threshold for that zone, the control system opens the fluid valve associated with that pressure zone to allow fluid to escape from the fluid cell into the fluid reservoir or another cell at a controlled rate. Similarly, when the control system detects a measured pressure that is less than the lower pressure threshold for that zone, the control system opens the fluid valve associated with that pressure zone to allow fluid to enter into the fluid cell from the fluid reservoir or another cell at a controlled rate.

The pressure sensing circuitry and control system are preferably powered by a common, conventional battery supply. However, other suitable power sources may be used, as known to those of skill in the art. The power source may be located within the insert. It is envisioned that the power source may be located on the prosthetic device at any location that does not negatively affect the performance of the device.

In one embodiment, a typical cycle will comprise a change in pressure applied to one or more of the cells in the array 302, thus causing a pressure to be read by a pressure sensor 314, and then sent to the CPU 304. In a case where the CPU determines that an increase in a pressure of a cell in the array 302 is necessary, the CPU will send a signal to the valve manifold 312 to select the appropriate fluid line. The CPU will then send a signal to the pump motor 310, thus causing a fluid displacement from the fluid reservoir 316 toward the desired cell 302 in the array via the valve manifold 312, the manifold having been appropriately set to direct the fluid to the appropriate cell.

Those skilled in the art will recognize that the control system may employ appropriate software having a user interface adapted to allow the system to be adjusted by a practitioner or an end user. Those skilled in the art will understand how to configure such a software system if one is desired.

Manual Control System

Alternatively, the amputee may control at least a portion of the system. For example, the amputee may control the initial pressure of the insert by manually pumping the bladder system to a pressure that is comfortable to the user for a particular activity. After pumping the bladder system manually, the control system as described may control the pressure of the system, or, alternatively, the user may continue to control the system by manually adjusting the pressure in the entire system, each zone, or, alternatively, each individual cell.

In one example of manual operation, an amputee may desire to open a central valve to all of the cells, or multiple vales to cells of different zones, to provide fluid into those cells or zones of cells. A manual pump may be provided for directing fluid into those cells. As an amputee needs more volume support, he can just open a valve manually to cause the cells to inflate. In one embodiment the amputee can selectively choose which zones require more fluid.

In another example, manual control is advantageous when an amputee desires to walk down a hill or a slant. In an embodiment where all the cells are interconnected, as the amputee walks down the hill all of the fluid will flow to the bottom. Thus, in one embodiment, an amputee is provided with manual control to close off or isolate fluid in cells near the top of the stump such that fluid can be maintained in the upper portion and provide adequate support. Alternatively, passageways near the top of a socket can be made smaller such that it takes longer for fluid to migrate down from a top of a cell.

Cell Embodiments

Figure 4:
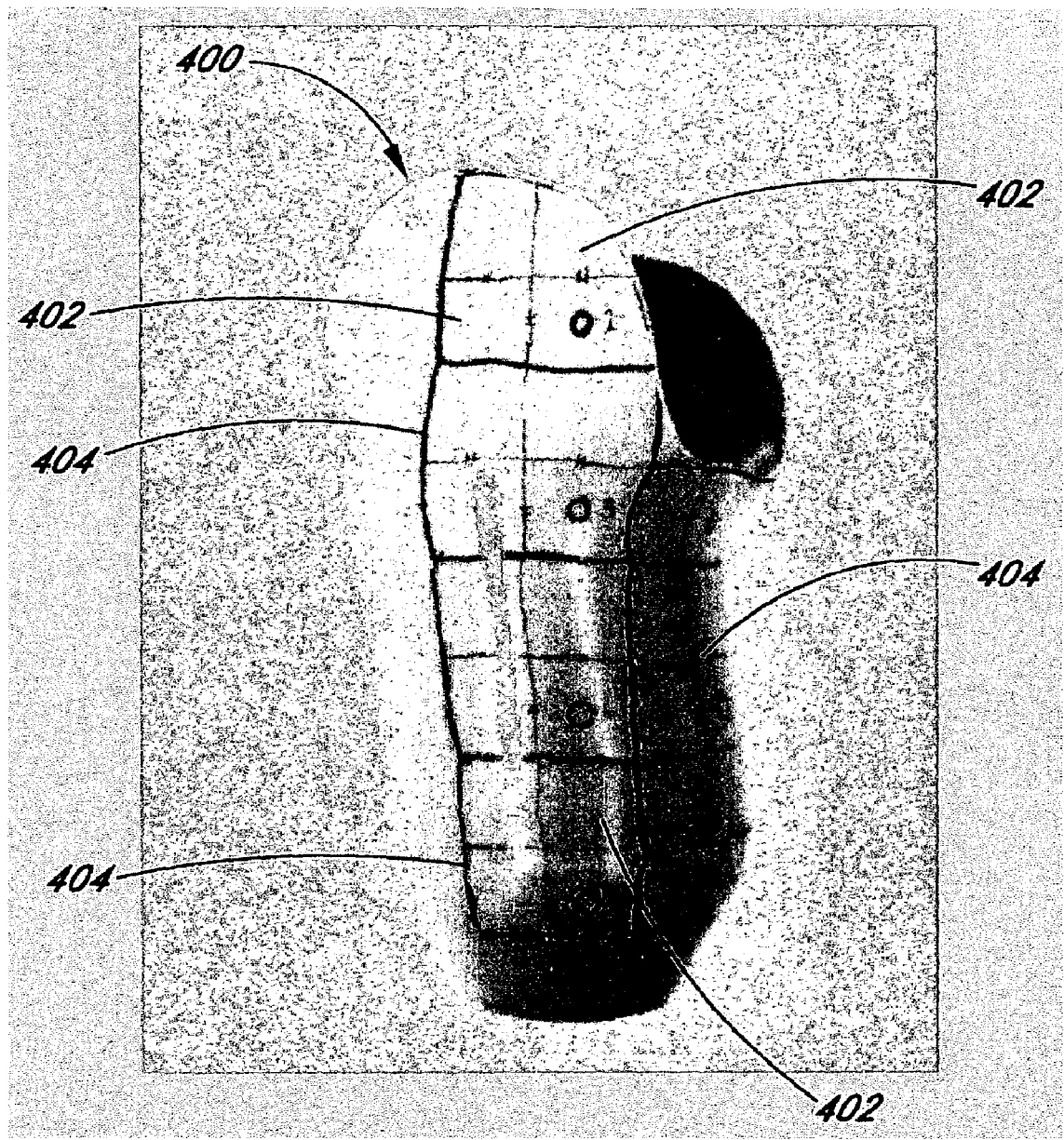
FIG. 4 is a perspective view showing a socket having a bladder system according to one preferred embodiment.

The socket system 400 of FIG. 4 illustrates one embodiment of the location of a fluid cell pack to be provided on the interior of a socket, substantially covering the posterior half of the limb of the wearer, and includes a plurality of cell groups (e.g. zones) 404. In one embodiment, each cell group or zone 404 preferably includes 4 or more cells, more preferably 4-8 individual cells 402. More preferably, in one embodiment there are preferably four or more cells groups or zones, even more preferably 8 to 20 cells groups or zones, and even more preferably about 10 to 12 cell groups or zones, with a total of about 20 to 100 cells, more preferably about 40 to 50 individual cells. The exact number of cell groups and the shape thereof will be determined according to the specific needs of the limb region.

The large number of cells advantageously allows for more precise volume control to specific areas of the residual limb. Moreover, it is advantageous to use a larger number of small bladders, as opposed to using a single or few large bladders, because when pressure is exerted on a single large bladder, fluid tends to be redistributed to other areas of the bladder, thereby causing unreliable volume control. For example, when a larger bladder is used, a portion of the limb pressing against the bladder might press substantially all the way through the bladder and against the wall of the socket, due to the fact that fluid within the bladder is redistributed to other locations of the bladder. By contrast, with small bladders, the fluid within the bladders has less room to travel away from the point of pressure, thereby ensuring that a portion of the residual limb pressing against the bladder is received by fluid within the bladder. Thus, small bladders, even when interconnected with other small bladders, maintain fluid volume more effectively. This is because even when such small bladders are interconnected, the fluid passageways between bladders remain small to control the rate in which fluid is transferred.

In one embodiment, bladders or cells are relatively small and have a maximum dimension (preferably measured when laid flat against a surface, such as the surface of a socket), of about 2" or less. More preferably, the maximum dimension of a bladder is about 1¾" or less, more preferably about 1½" or less, even more preferably about 1¼" or less, and even more preferably about 1" or less. The thickness of the walls of a cell in one embodiment is between about 0.005" and 0.01". A cell not filled with fluid can have a thickness of about 0.2". When fully filled, the cell in one embodiment may have a thickness up to about 0.275 or up to about 0.3" or more, and when compressed, the cell in one embodiment may compress to a thickness of about 0.125" or 0.1" or less.

Preferably, the cells are positioned at the posterior portion of the socket only, as shown in FIG. 4. It has been discovered that the posterior portion of the residual limb has a greater volume fluctuation compared with other portions of the residual limb. This is due at least in part because the posterior portion contains more muscle and tissue, as compared to the more bony anterior portion of the residual limb. Accordingly, cells positioned at the posterior portion of the socket provide the required support for the residual limb during volume fluctuation, such that the feel of the socket and prosthetic device does not change significantly despite the volume fluctuations of the limb.

Figure 6:
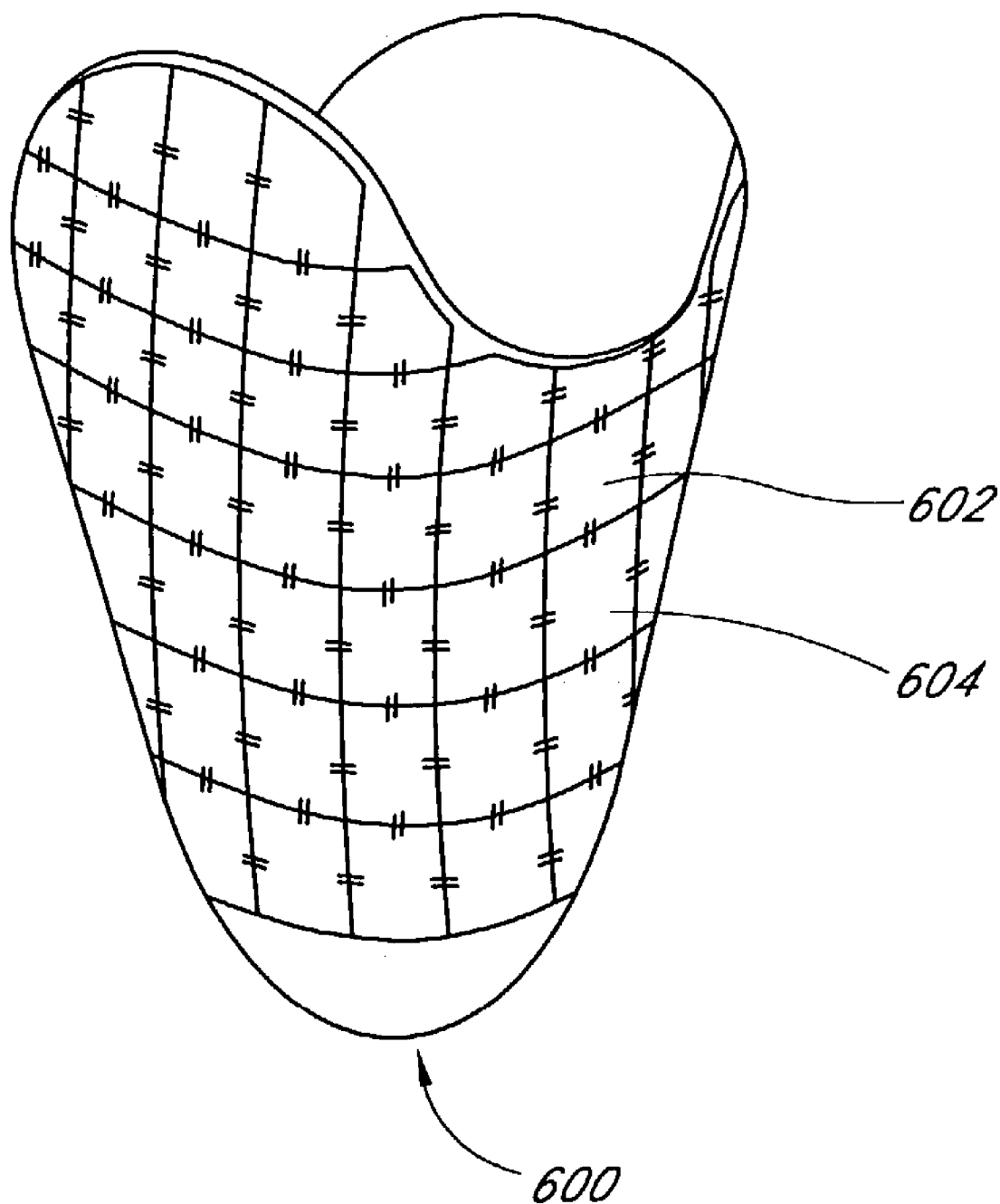
FIG. 6 is a perspective view showing a socket having a bladder system according to another preferred embodiment.

Alternatively, the cells may extend around the entire socket as shown in FIG. 6. For example, the anterior portion of a residual limb, even though it is bony, has a particularly contour. Accordingly, cells may be desirably positioned around the bony protuberances of the anterior residual limb to provide desired volume control. This is particularly desired due to the fact that the arrangement of the tibia and condyles will change during dynamic movement of the stump, for example, during flexion and extension.

Figure 5:
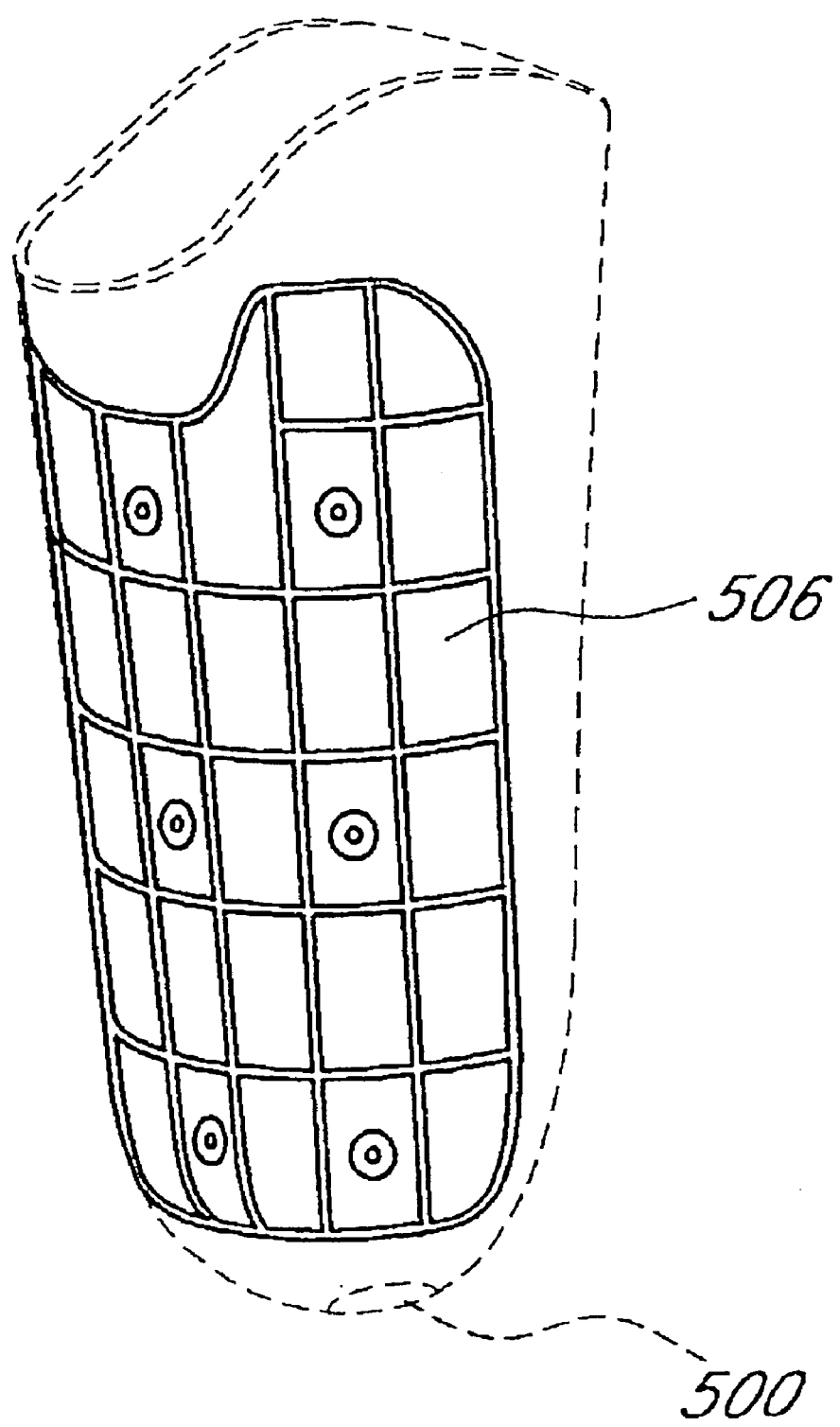
FIG. 5 is a perspective view showing a socket having a bladder system according to one preferred embodiment.

In one embodiment, as shown in FIG. 5, in addition to the cells 506 at the posterior portion of the socket, one or more cells can be provided at the bottom of the stump. The cell arrangement is substantially the same as the cell arrangement of FIG. 2B, with the addition of a cell 500 provided at the bottom of the socket. This cell 500 is preferably provided with a pressure sensor in order to sense sliding of a stump toward the bottom of the socket. Alternatively, a pressure sensor alone can be provided at the bottom of the socket. When the pressure sensor at the bottom of the stump senses additional pressure due to the sliding of the stump, it can activate fluid to flow into cells or zones of cells near the top of the stump, thereby creating more volume at the top to hold the stump in place.

As described above, in one embodiment at least the anterior portion of the interior of the socket is desirably contoured to conform to the shape of the residual limb, and a pressure sensor is provided at the bottom of the socket. If the pressure detected by the sensor increases, thereby indicating that the stump is slipping, zones in the posterior portion of the socket can be activated to increase the pressure as desired to press the stump correctly into position against the contours of the anterior portion of the socket. As described further below, the control system can be used to activate and adjust fluid volume in various zones of bladders in the posterior portion of the socket to create the appropriate volume control.

FIG. 6 shows another embodiment of a socket insert 600 having a plurality of cells 602 positioned around substantially the entire surface of the insert. A system of fluid passageways 604 is provided to connect the cells to one another in an array. For the embodiment of FIG. 6, the cells may also be organized into zones which may or may not be interconnected, as described below.

Figure 7:
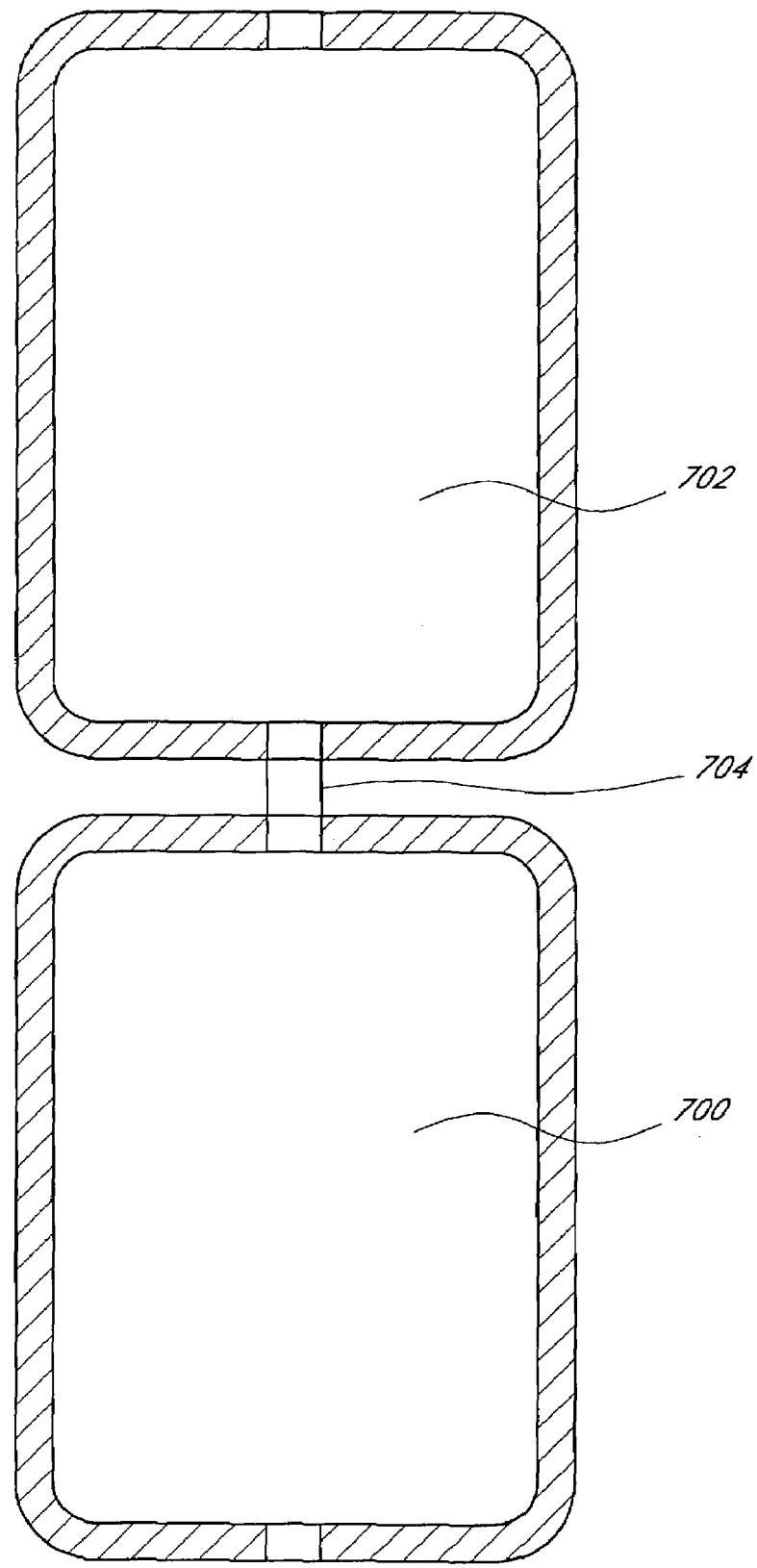
FIG. 7 is a cross-sectional view showing a pair of bladders.

FIG. 7 shows a detailed view of two interconnected cells 700, 702. These cells can be adjacent cells within an individual zone. Fluid cells 700, 702 are connected by passageway 704. Cells 700, 702 are preferably filled with a fluid medium. Fluid may flow from cell 700 to cell 702, or vice versa, due to pressure exerted on a cell, from a point of high pressure to low pressure. In a preferred embodiment, the passageway 704 is open, such that pressure applied to cell 700 causes fluid to flow naturally to cell 702. In an alternative embodiment, valves can be provided within passageways between individual cells to provide more active control of fluid flow. These valves could be controlled using the control system or manual control as described above. Although the cells 700, 702 are shown as being in fluid communication with each other, it is envisioned that cells 700, 702 may be in fluid communication with other cells within an individual zone or to cells throughout the entire system.

Figure 8:
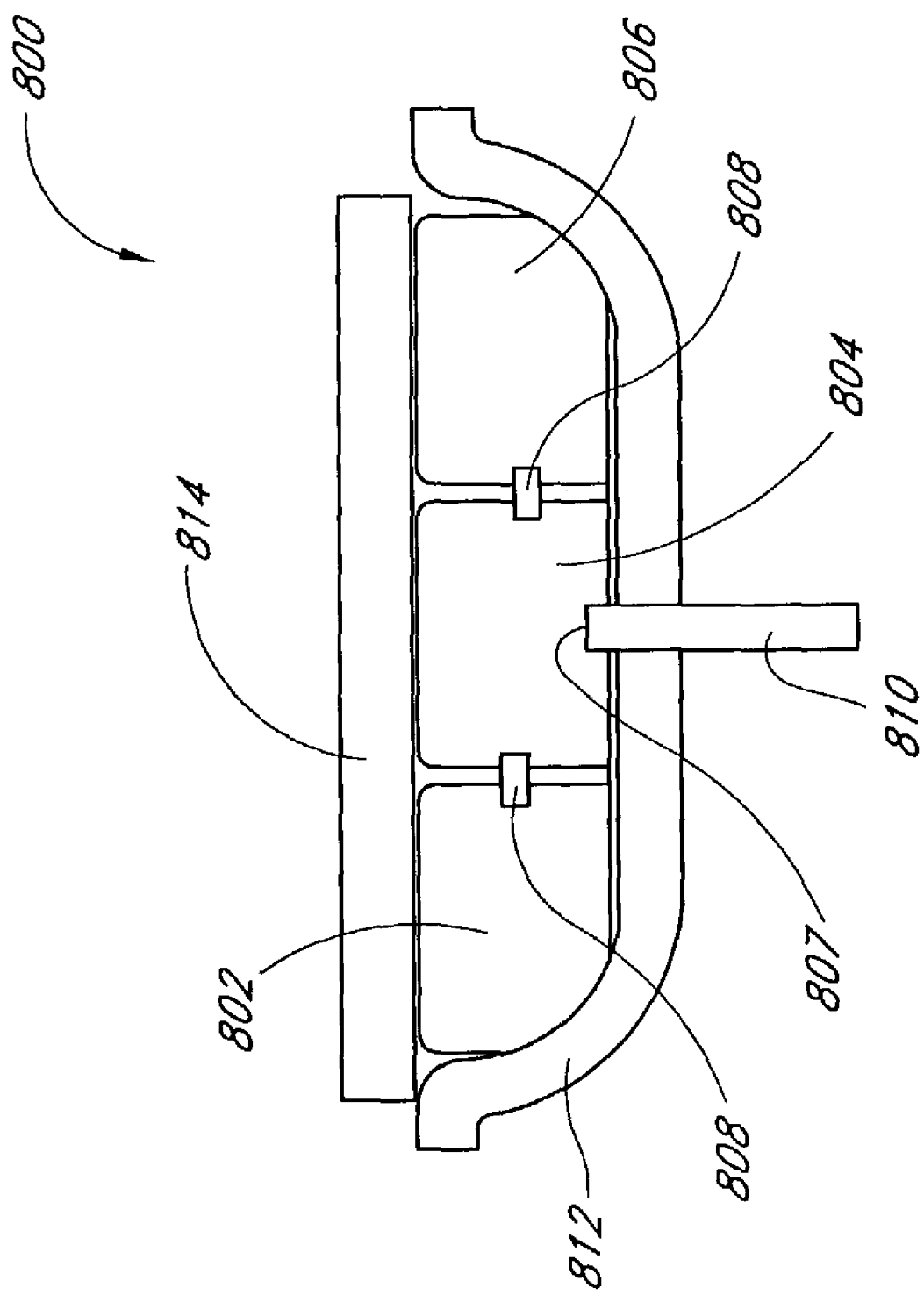
FIG. 8 is a cross-sectional view showing a plurality of bladders within a zone.

FIG. 8 schematically shows a cell pack or zone 800 comprising first 802, second 804 and third 806 cells joined in fluid communication with one another by interconnecting tubes 808 within a recess of socket 812. The cell pack 800 is preferably made of a tough, flexible urethane material molded into closely nested individual cells 802, 804, 806. Each cell group has a tube connection port 807 and is fed by a single fluid line 810 (corresponding to fluid lines 210 of FIG. 2A). This fluid line 810 connects the cell group or zone to the control system as described above. Fluid is shared between cells within a group by micro-interconnecting tubes 808. FIG. 8 also shows a liner 814 sealing the cell pack 800 between itself and the socket wall 812.

The fluid medium within the cells is preferably a fluid, such as a liquid or gel. The preferred fluids exhibit non-resilient, non-restoring properties typical of plastic or viscous thixotropic materials which flow gradually when pressure is applied to them but which maintain their shape and position in absence of pressure. Other fluids such as water, gels, oil, or grease can also be used. The viscosity of the fluid should be sufficiently low that fluid can pass through the valves and interconnecting tubes of the system. Additionally, each cell may only be partially filled with fluid so that there is no distending or tensioning in use.

In a preferred embodiment, the cells are manufactured out of a thin, flexible, suitably strong, lightweight moisture and vapor impervious material, such as polyurethane, silicone or other materials. Though other materials having similar characteristics can be used, and indeed are contemplated, the remainder of the discussion will refer to the preferred material, polyurethane. The cells may all be the same size or, alternatively, each cell may be a different size. The number and arrangement of the cells is dependent on the individual needs of the amputee. Furthermore, the cells and zones may be arranged symmetrically or, alternatively, the cells and zones may be in a staggered arrangement.

As described with respect to FIGS. 2A-2C and FIG. 8 above, each zone may preferably have its own valve for fluid communication with the control system. Alternatively, a central valve may be provided for the entire system of cells when all of the cells are interconnected. In another alternative embodiment, each cell may be independently inflatable and provided with an inflation valve in the wall thereof. Alternatively, a valve may be attached at the end of tubing extending from the wall of the compartment.

Figure 9:
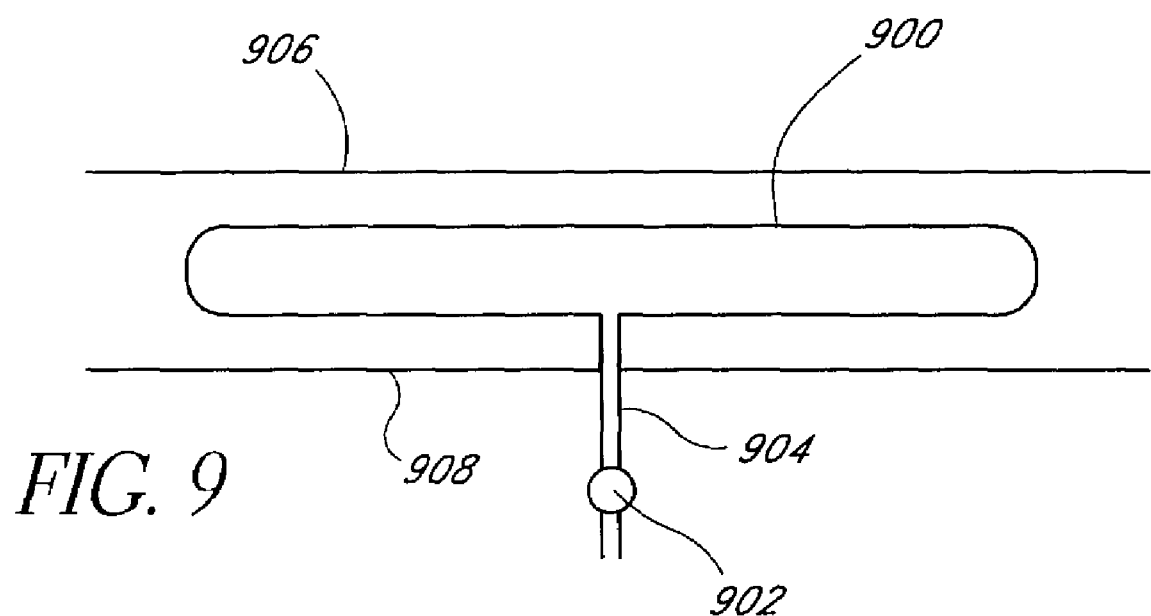
FIG. 9 is a side view showing a bladder having a fluid control valve connected thereto.

FIG. 9 shows a side view of a cell 900 and an associated valve 902 to illustrate one embodiment of the operation of the device. Although the cell 900 of FIG. 9 is shown as being independently inflatable and separated from one another, it will be appreciated that these cells may also be interconnected with other cells. Thus, the valve 902 may be a central valve for an entire system of cells, the valve for a particular zone, or simply an individual valve for each cell. When the valve 902 is a central valve, each of the bladders 900 would have a fluid duct (such as fluid duct 808 in FIG. 8) interconnecting adjacent bladders. Wall 906 represents an interior wall of the socket insert, in contact with socket liner 218 (FIG. 2C), while wall 908 represents an exterior wall of the socket insert, in contact with socket 200 (FIG. 2A). In the embodiment shown, the valve is provided along passageway 904 which extends to the outside of the socket. It will be appreciated that the valve can also be provided on or in the wall of the cell, and in other configurations as well.

The fluid in the cell 900 of FIG. 9 is preferably non-compressible, such that even when an external pressure is applied to the cell, it does not compress and is able to hold its volume. The fluid exits valve 902, or may exit through a fluid duct (not shown) to an adjacent cell. When a pressure sensor is used associated with the cell 900, the flow of fluid through valve 902 is based on readings from the pressure sensor and controlled by the CPU, as described above.

Although there may be a number of different ways to make the cells, they are preferably made from a vacuum forming technique. Vacuum forming with plastic typically comprises heating a plastic sheet to a temperature under the melting point, then lowering the plastic sheet over a pattern at the same time air is withdrawn from between the plastic and the pattern. When the air is withdrawn, a vacuum is created, and the plastic sheet is pressed to the pattern by atmospheric pressure. The plastic is then cooled and the pattern retracted leaving the plastic to set to shape. Vacuum forming can be used to form cells having curved side walls, such as shown in FIG. 9. In such an embodiment, a cell is preferably formed by attaching two half-cells together. In another embodiment, vacuum forming can be used to form cells having vertical side walls, or even slanted side walls which point toward the center of the cell. Particular shapes of cells are further shown in FIGS. 17-21 below.

Vacuum forming is a preferred method of manufacture for small production runs because the process is more cost effective than injection molding. However, injection molding or other known methods of manufacturing bladders may also be used, as known to those of skill in the art.

Active System

Figure 10:
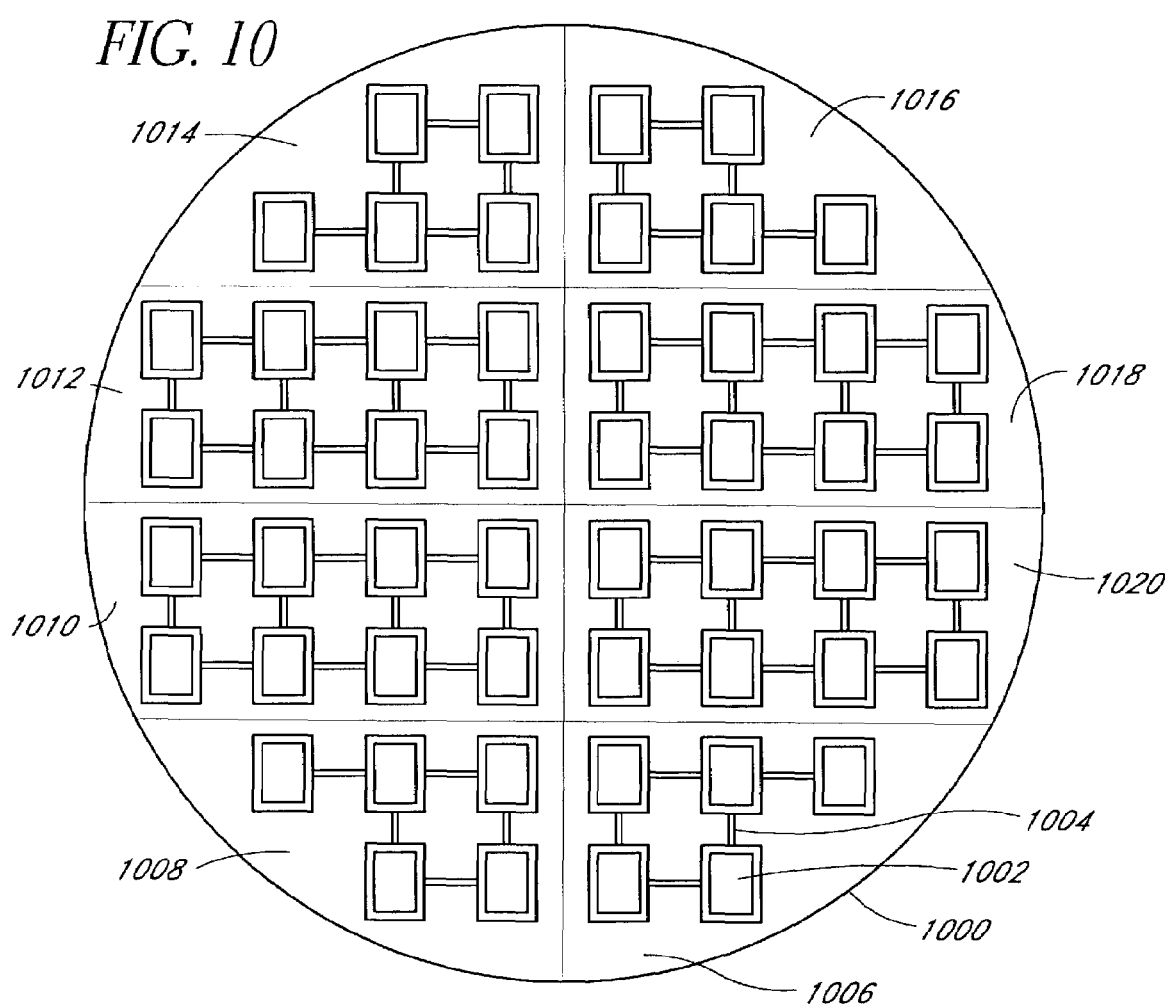
FIG. 10 is a schematic view of a socket insert having an active system.

FIG. 10 is a schematic illustration of an insert 1000 having a plurality of inflatable bladders in a so-called "active system." The insert 1000 is shown having a circular shape for illustrative purposes only, and it will be appreciated that the insert can take any suitable shape for being positioned within a socket. The actual shape provides optimal comfort for the amputee and is adapted to fit comfortably within the socket. Fluid cells 1002 form part of the fluid pressure system. Each fluid cell 1002 is essentially an empty pouch formed in the insert. Fluid cells 1002 are shown substantially separated from one another for exemplifying purposes. It is envisioned that the cells 1002 may also be in direct contact with one another, or may share common walls.

Each cell of the active system is preferably provided with a corresponding fluid supply valve (not shown, corresponding to valve 208 of FIG. 2A) and a supply conduit (not shown, corresponding to conduit 210 of FIG. 2A) in order to connect each cell to the control system. In addition, an individual pressure sensor is provided for each cell, such that the control system can control the volume of every cell based on the pressure exerted by the user's limb on the fluid cell. As the pressure increases over a threshold, a control system (either automatic or manual) opens the valve to allow fluid to escape from the fluid cell.

The cells of FIG. 10 are preferably organized into zones. The fluid passes through channels 1004 between the cells within each zone, the flow within these channels being preferably controlled by an optional valve contained therein and the control system described above. In another embodiment, no channels 1004 are provided, and each cell is independent of another. In yet another embodiment, the channels remain open, such that fluid can flow naturally between the cells within a zone (see the semi-active system, described below). In yet an alternative embodiment, described below, the zones may also be interconnected, such that fluid may flow from one zone to another zone (see the semi-active system, described below).

As illustrated, the insert in one embodiment has 8 zones 1006, 1008, 1010, 1012, 1014, 1016, 1018 and 1020, with 4 to 9, more preferably 5 to 8, cells per zone. The actual number of zones and cells may vary depending on the amputee's requirements.

The supply conduits (not shown) preferably connect each fluid cell of each zone with a central fluid reservoir. Alternatively, each zone may have its own reservoir. The fluid valves contained in the supply conduits are preferably adjustable over a range of openings to control the flow of fluid exiting the fluid cell and may be a suitable conventional valve such as a solenoid valve or other valves as described above. The valves in the active system embodiment are preferably solenoid valves.

Consequently, the prosthetic device may be self-adjusting as the pressure changes by regulating the flow of fluid out of each fluid cell. The insert senses pressure changes, distributing the pressure felt by the amputee in the presence of volume fluctuations. An adjustment control may also be provided to allow the user to adjust or scale the amount of pressure provided, as described above.

Passive System

Figure 11:
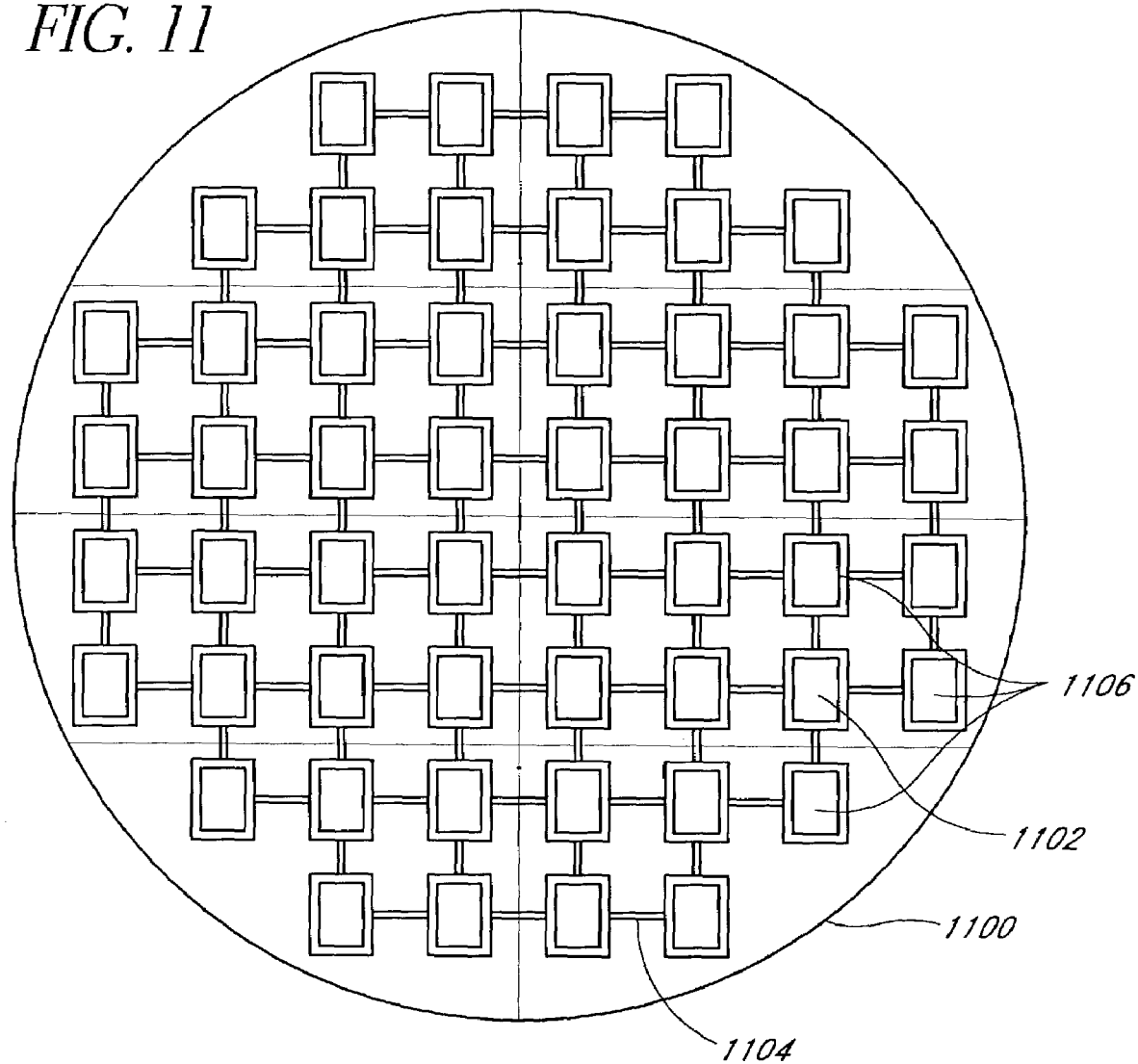
FIG. 11 is a schematic view of a socket insert having a passive system.

In a "passive system," as shown schematically in FIG. 11, the insert 1100 has a system of fluid cells 1102 which are each positioned in an interconnected array. The insert 1100 is shown having a circular shape for exemplifying purposes. The actual shape provides optimal comfort for the amputee and is adapted to fit comfortably within the socket. The fluid cells are in fluid communication with each other via a series of channels 1104. Fluid cells 1102 are shown substantially separated from one another for exemplifying purposes. It is envisioned that the cells 1102 may also be in direct contact with one another, or may share common walls.

A fluid supply valve and fluid flow passageway is preferably connected at one end to any one cell, such as cell 1102, and at its other end to another cell or to a pump (not shown). This tube preferably serves as a central line for all of the cells. The cells are then inflated with a fluid to the desired size and pressure. During inflation, the fluid will sequentially and expansively flow from one cell to another in the array.

The channels 1104 are preferably large enough such that fluid can flow between cells 1106, but are not so large that the cells 1106 can become fully deflated due to pressure changes. The size of the channels can preferably be selected to maintain a desired flow rate for fluid from one cell to another, based on the viscosity of the fluid used. In one embodiment, the flow rate should be selected and configured such that fluid can flow from one cell to another, or from one end of a zone to another end of the same zone, in about one second or more. More preferably, a longer flow rate, for example of about 2 to 3 seconds, for migration of fluid from one cell to another, is desired to ensure that fluid does not flow too quickly.

The cells may be further organized into zones, such as described above. In the system where the cells are organized into zones, the fluid passes through orifices between the cells within each zone. The zones are also interconnected, such that fluid may flow from one zone to another zone. Valves may be provided between cells of a zone, or between adjacent zones, to control the flow of fluid therebetween. Such valving can be controlled by adjusting the size or shape of the conduit between cells or zones, such that in one example, fluid flow between cells occurs more readily than fluid flow between adjacent zones.

In the passive system embodiment of FIG. 11, pressure sensors are not necessarily provided for individual cells or zones because the insert itself is a pressure sensing device. The bladder system senses regions of fluid at high pressure due to volume fluctuations of the residual limb, and moves the fluid to an area of low pressure passively. Accordingly, the monitoring of the pressure within the cells or zones is inherent to the system, and does not require an external system for monitoring and compensating for the volume fluctuations of the residual limb. However, it will be appreciated that such pressure sensors can still be provided.

It will further be appreciated that the cells of a zone themselves can be used as pressure sensors by detecting the amount of fluid that flows in and out of a zone. In such an embodiment, an in-line sensor can be provided in a tubing going toward or away from the zone. This in-line sensor utilizes the fluid flow to or from the zone to detect pressure changes, and transmits this information to the control system.

Semi-Active System

Figure 12:
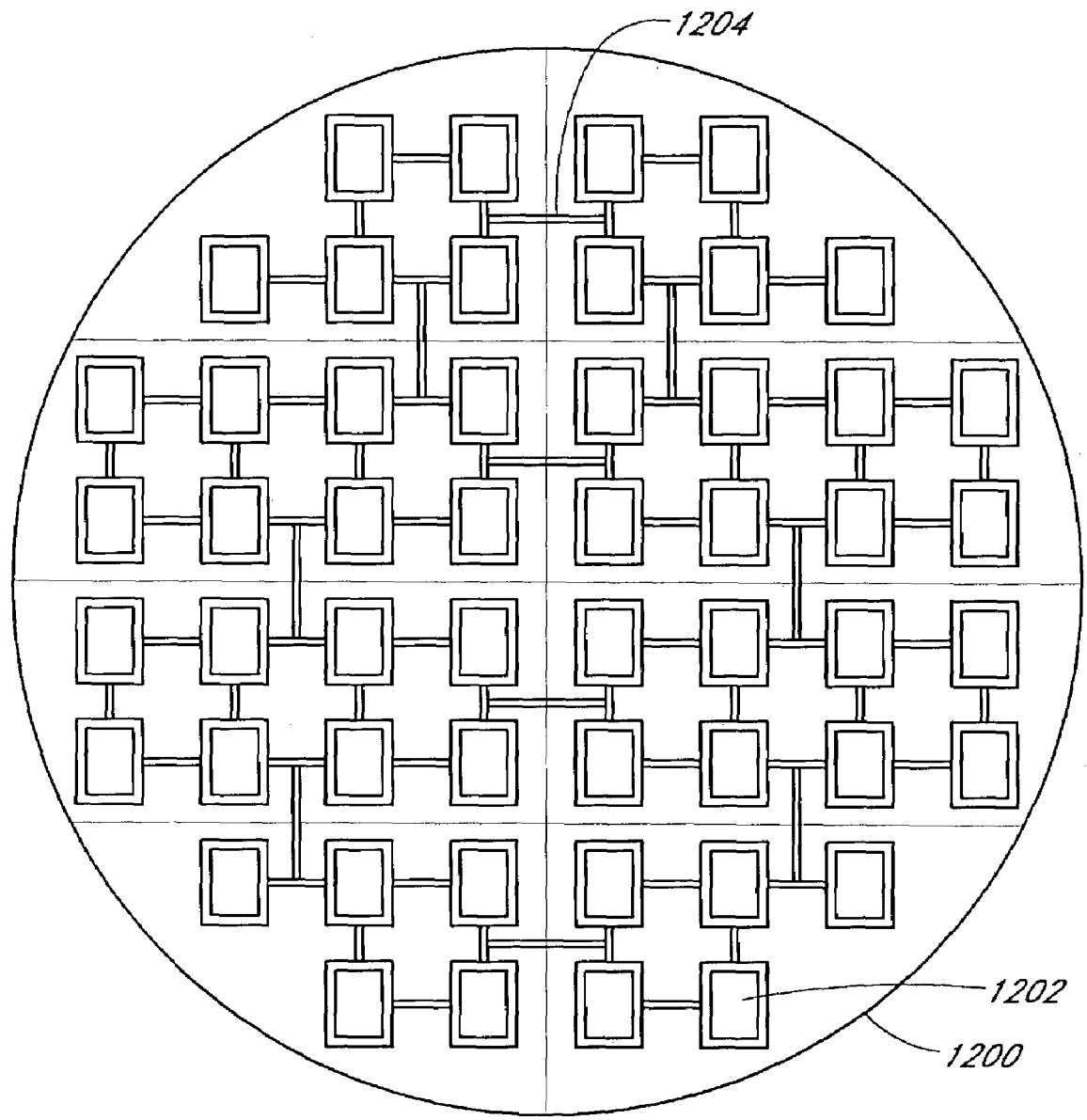
FIG. 12 is a schematic view of a socket insert having a semi-active system.

The semi-active system as shown in FIG. 12 is a combination of the passive and active systems previously described, and similar to the embodiments shown in FIGS. 2 and 3. In the semi-active system, the individual zones each contain a plurality of interconnected bladders 1202, connected via a fluid supply valve (not shown) for each zone to a pressure sensing system and fluid reservoir (either a central reservoir or a reservoir for each zone). The cells within each zone are interconnected through an orifice system such that each zone can be individually controlled. Furthermore, adjacent zones may also be interconnected by fluid ducts 1204, with or without fluid supply valves therein, such that fluid can flow between adjacent zones due to pressure differences.

Similar to the active system described above, the cells of the semi-active system are preferably organized into zones, typically comprising 4-9 cells each. More preferably, there are 8 zones, with 5 to 8 cells per zone. The actual number of cells and zones will vary depending on the amputee's needs. The fluid passes through channels between the cells within each zone.

A fluid duct (not shown) preferably connects the fluid cells of each zone with a fluid reservoir. Similar to the embodiment shown in FIG. 8, one fluid duct can be provided for a plurality of bladders within a zone, supplying fluid to and from a central reservoir. Alternatively, each zone may have its own reservoir. A flow regulator, which in this embodiment is a fluid valve, is disposed in the fluid duct to regulate the flow of fluid through the fluid duct, such as shown in FIG. 9. The fluid valve is adjustable over a range of openings to control the flow of fluid exiting the fluid cell and may be a suitable conventional valve such as a solenoid valve. The valves are preferably solenoid valves.

During inflation of a cell connected to a fluid duct, the fluid will sequentially and expansively flow from one cell to another in the array within the zone through the conduits interconnecting the cells within a zone. Each zone preferably includes a pressure sensing device, which measures the pressure for each zone. The pressure sensing system measures the relative change in pressure in each of the zones. The control system receives pressure data from the pressure sensing system and controls the fluid pressure system, such that fluid can flow in and out of the zone back to the fluid reservoir, or alternatively, to adjacent zones through conduit 1204.

Alternative Cell Shapes and Arrangements

Figure 13:
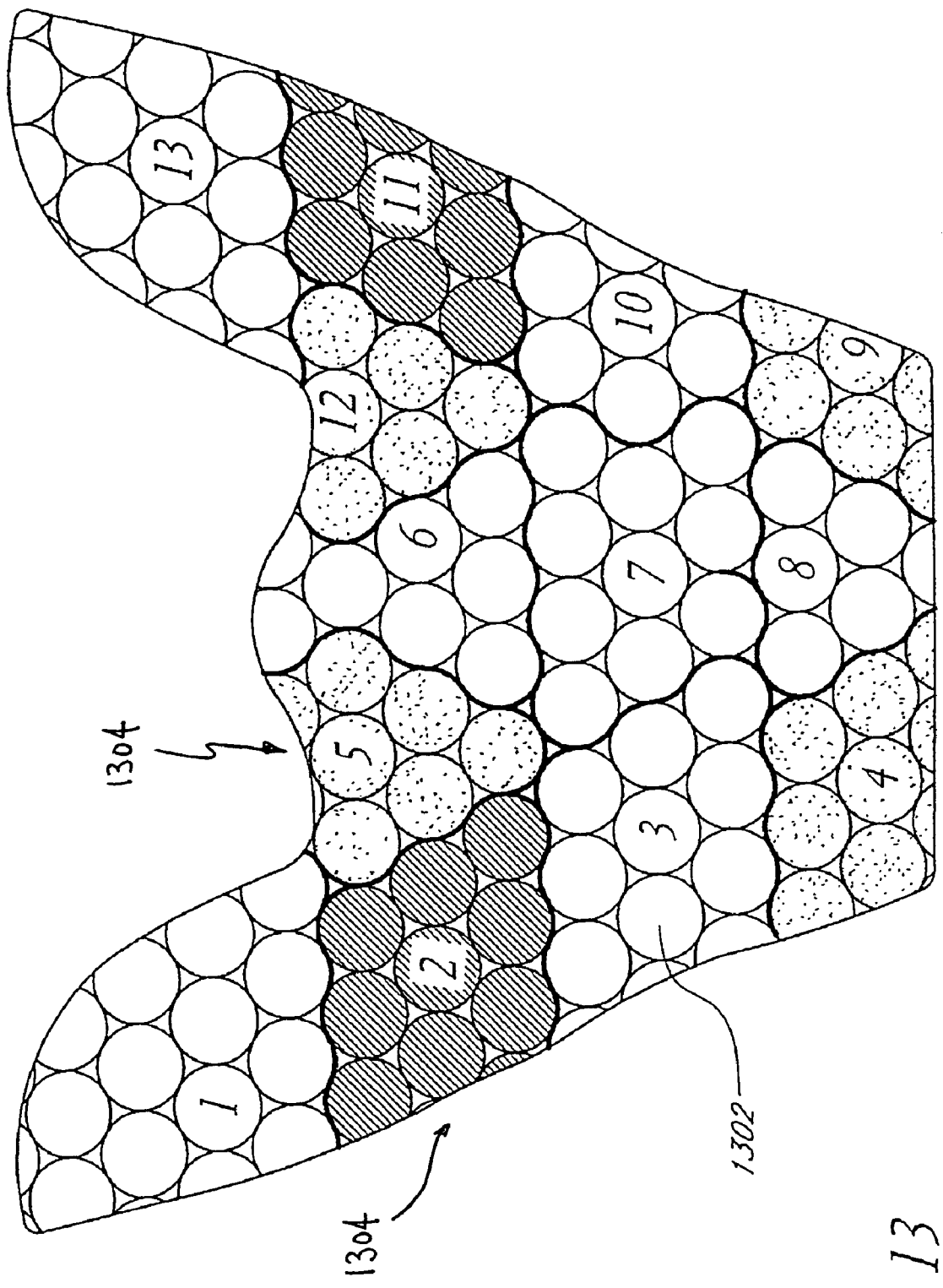
FIG. 13 is a schematic view of a socket insert having circular bladders.
Figure 14:
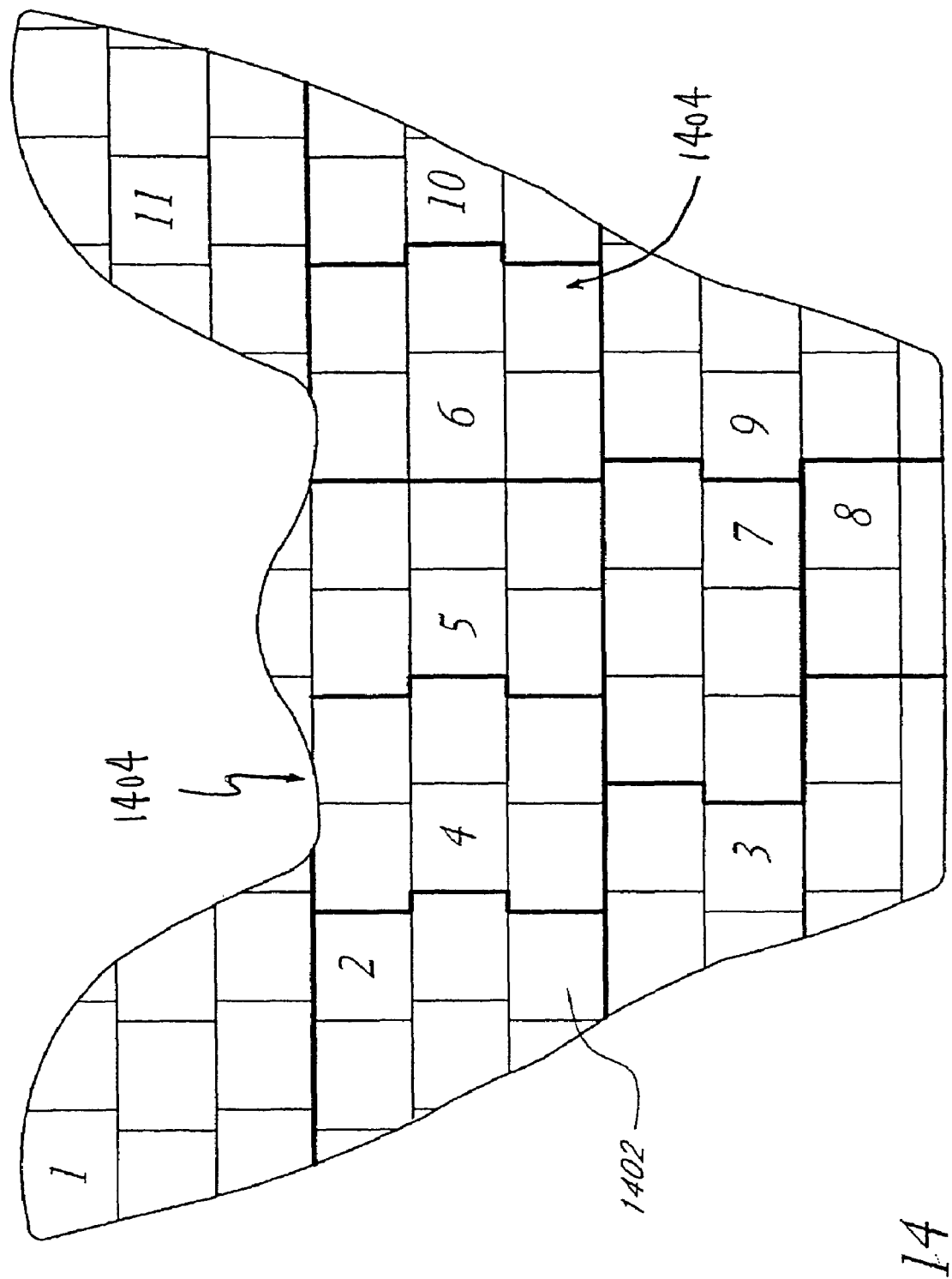
FIG. 14 is a schematic view of a socket insert having rectangular bladders.
Figure 15:
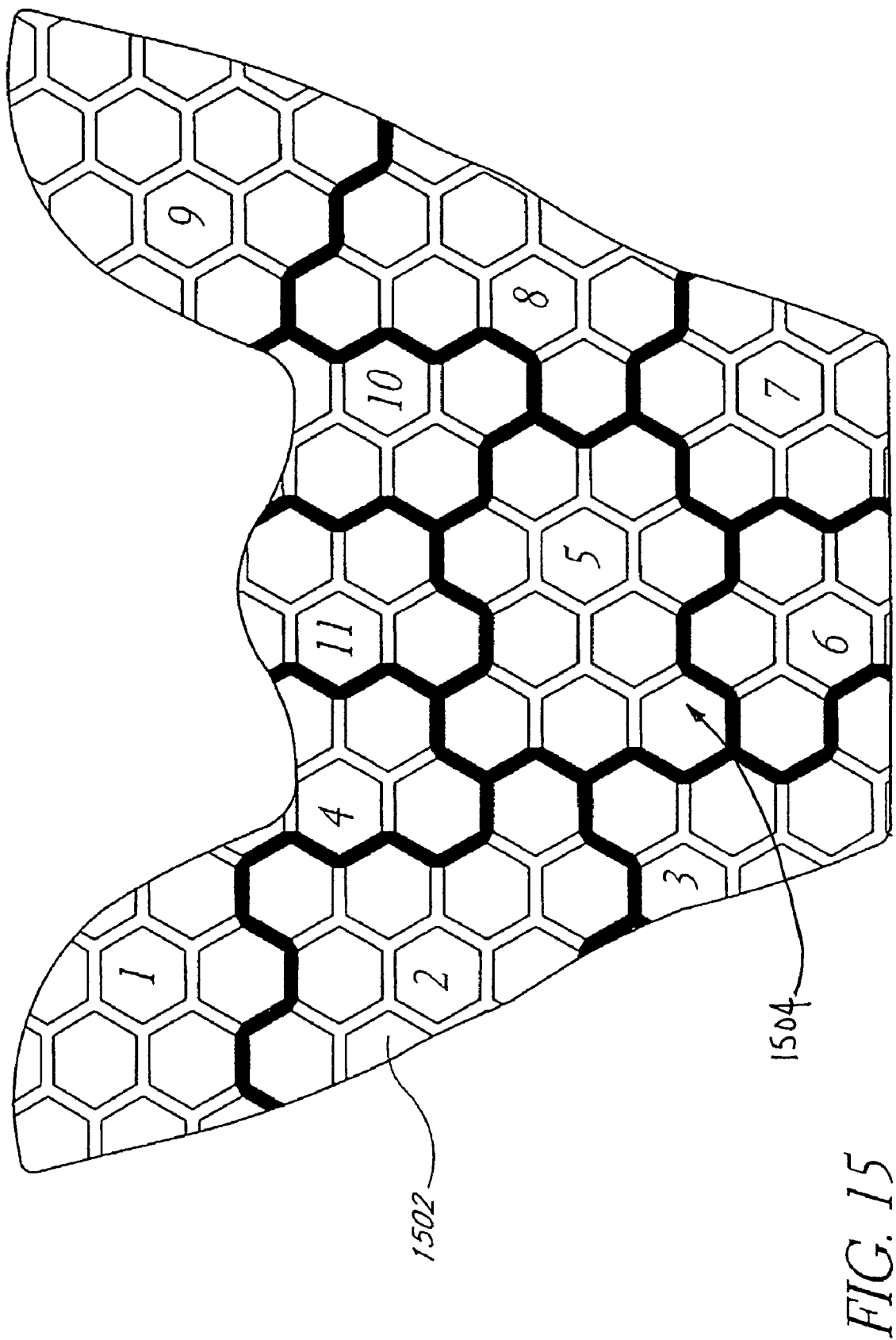
FIG. 15 is a schematic view of a socket insert having hexagonal bladders.
Figure 16:
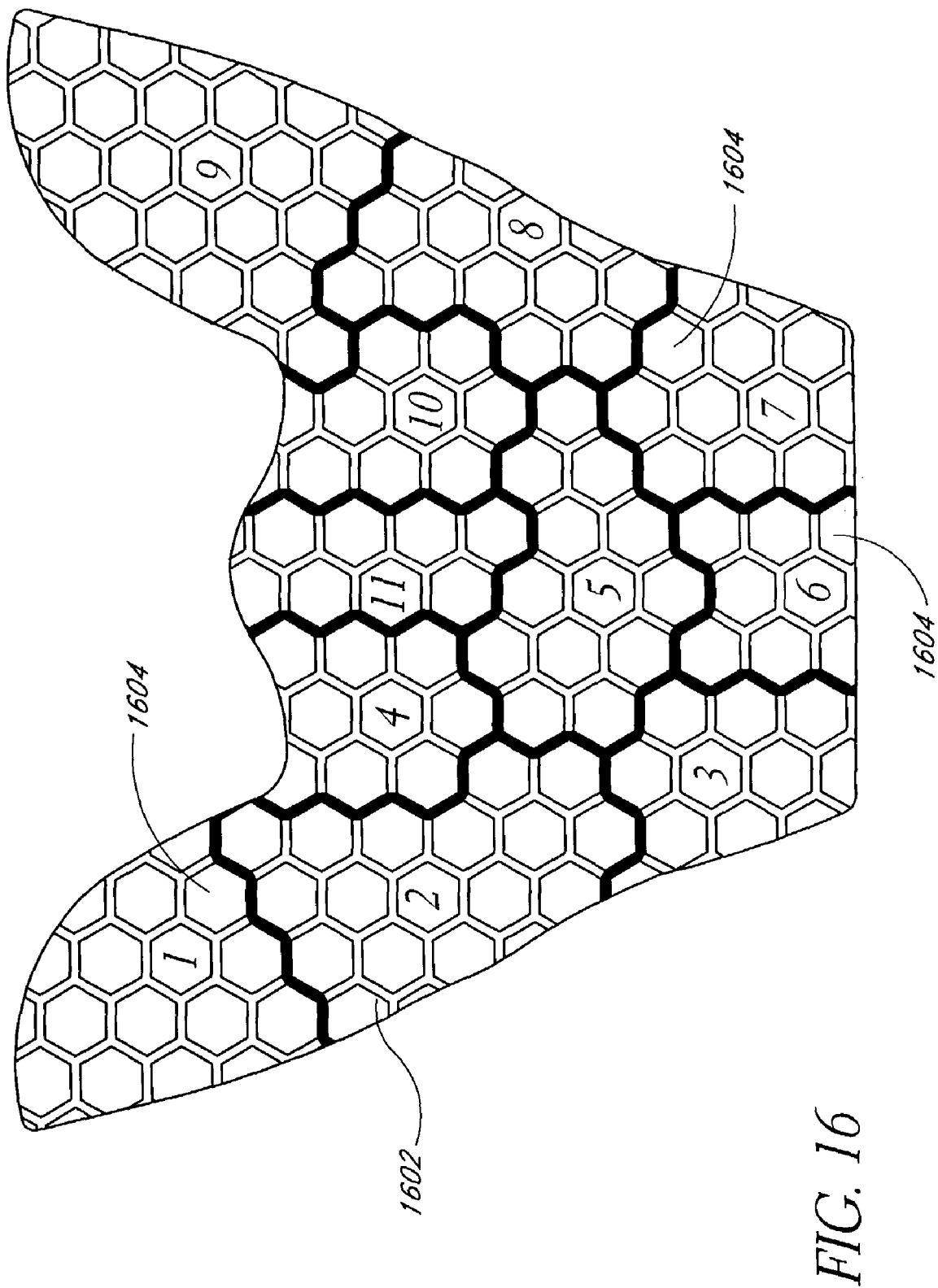
FIG. 16 is a schematic view of an alternative embodiment of a socket insert having hexagonal bladders.
Figure 17:
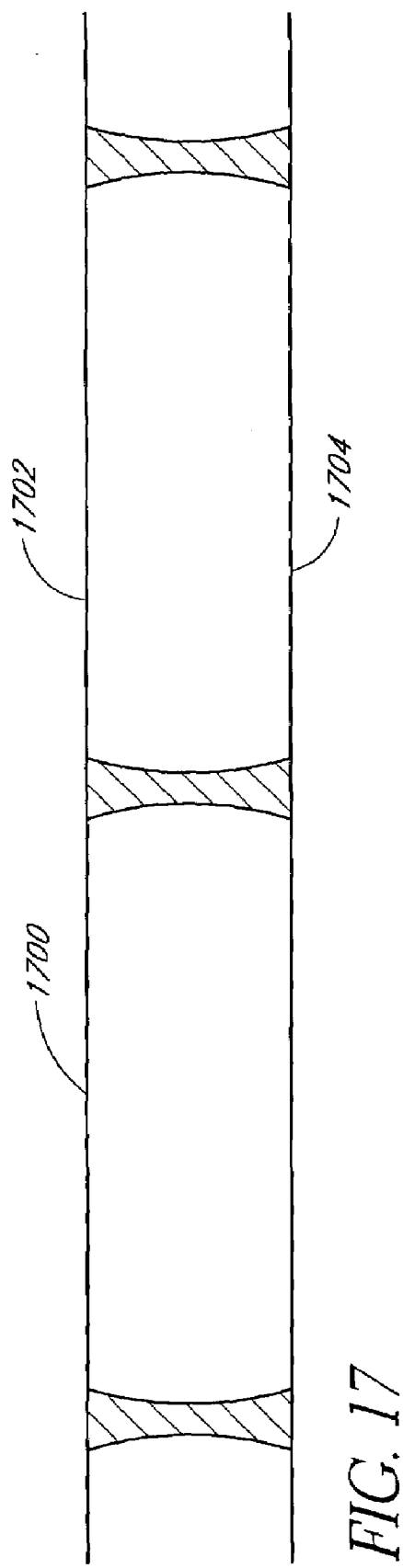
FIG. 17 is a cross-sectional view of one construction of the bladders of the socket insert of FIGS. 2A-C.
Figure 18:
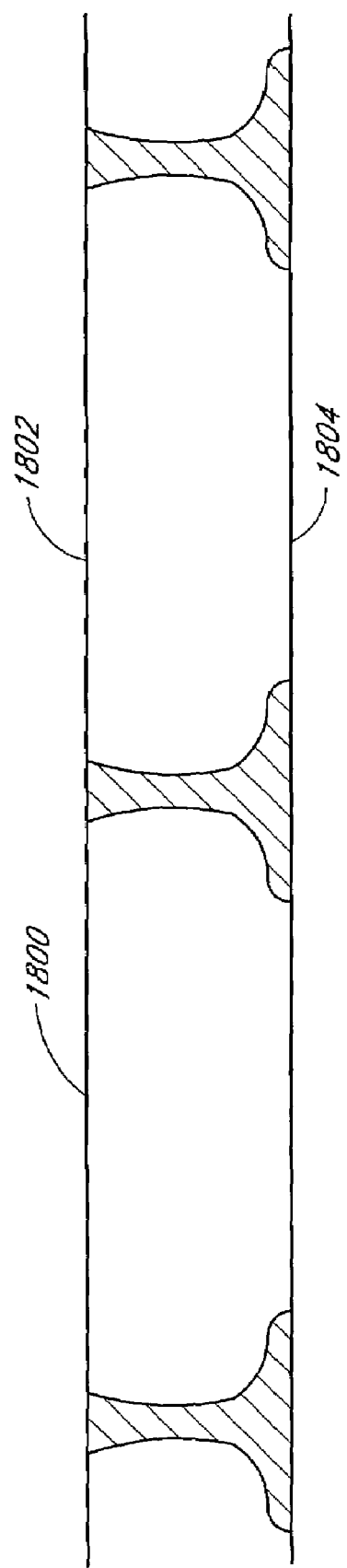
FIG. 18 is a cross-sectional view of another construction of the bladders of the socket insert of FIGS. 2A-C.
Figure 19:
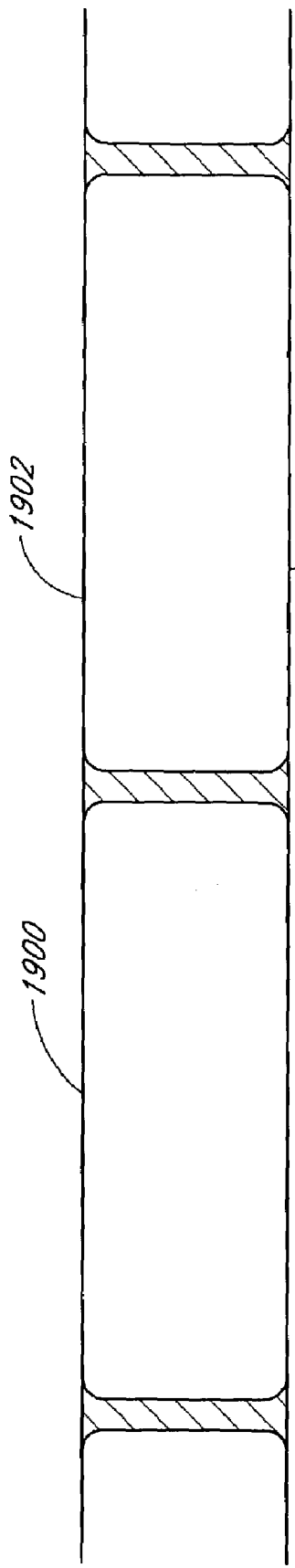
FIG. 19 is a cross-sectional view of another construction of the bladders of the socket insert of FIGS. 2A-C.
Figure 20:
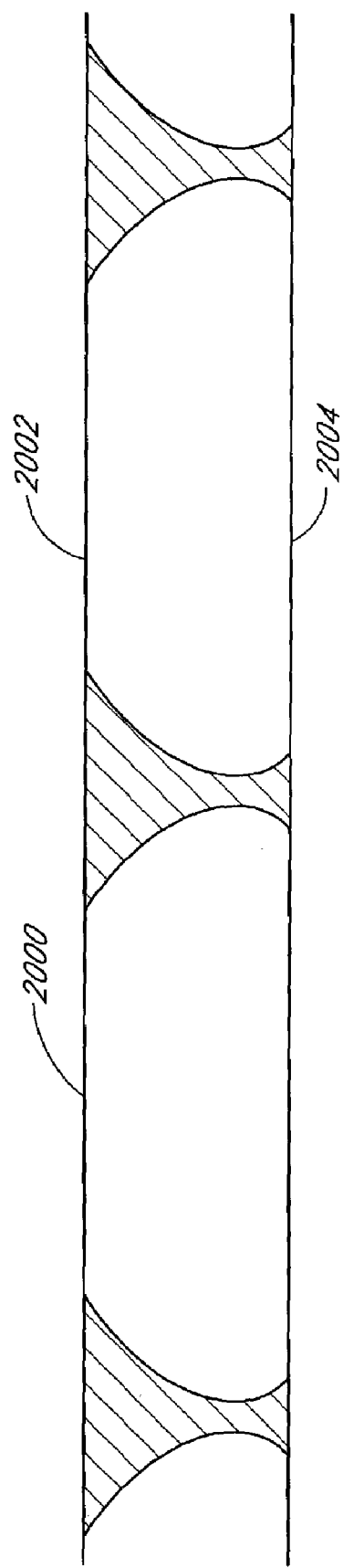
FIG. 20 is a cross-sectional view of another construction of the bladders of the socket insert of FIGS. 2A-C.

FIGS. 13-16 show alternative shapes for a cell pack (zones) and fluid cells (bladders) having desired features and advantages. FIG. 13 shows circular cells 1302 organized into substantially quadrilateral or triangular cell groups 1304. FIG. 14 shows rectangular bladder cells 1402 organized into substantially polygonal cell groups 1404. FIG. 15 shows hexagonal bladder cells 1502 organized into substantially polygonal cell groups 1504. FIG. 16 shows an alternative embodiment of hexagonal bladder cells 1602 organized into substantially quadrilateral cell groups 1604, wherein the individual cells have a smaller diameter.

The bladder systems shown in FIGS. 13-16 are merely schematic, and generally illustrate different shapes and arrangements of cells and zones. As previously described, the cells and zones may be staggered or symmetrical. The actual number of cells and zones may vary depending on the needs of the amputee and the dimensions of the socket or insert. For example, FIG. 13 shows an embodiment having 13 zones having 7-12 cells in each zone, while FIGS. 14-16 show an embodiment having 11 zones having 520 cells in each zone. Furthermore, the cells may extend to the periphery of the insert, as shown in FIGS. 13-16, wherein partial cells are provided at locations where there is not enough room for an entire cell. Alternatively, empty spaces may exist at locations where there is not enough room for an entire cell.

The overall shape of the insert as shown in FIGS. 13-16 is preferably adapted for desired positioning within the socket.

In one preferred embodiment, where bladders are desired to cover a posterior portion of the socket, the insert is substantially wing-shaped such that the winged portions of the insert provide additional coverage near the top of the socket along its sides.

Referring to FIG. 15 in particular, zones are preferably arranged to accommodate different muscle groups of the residual limb. For example, in one embodiment, zones 4, 11 and 10 are provided to correspond generally to the vascular bundle below the knee joint, corresponding to the gastroc muscle. In another embodiment, zones 4 and 10 correspond generally in location to the hamstring muscles. Thus, it may be desired to provide higher fluid pressures to the zones corresponding to these hamstring muscles as compared, for example, to zone 11. Moreover, near the bottom of the insert, for example in zone 6, it may be desired to provide additional pressure as compared to other zones, as stumps may tend to shrink near the bottom. In particular, as stumps may have no venous return supply, blood tends to accumulate near the bottom of the stump. Accordingly, zone 6 can be provided with additional fluid pressure as compared to other zones in order to get blood moving away.

It will also be appreciated that zones that experience greater volume fluctuations or experience higher pressures applied from the residual limb are preferably smaller than zones that experience smaller volume fluctuations or experience lower pressures applied from the residual limb. For example, zones 4, 11 and 10 in FIG. 15, described above, are preferably smaller than zones 1 and 9. This is because in zones 4, 11 and 10, the stump may apply a higher pressure to these zones, and therefore, the zones are smaller such that the fluid cannot flow away to other cells within the zone, which would then diminish the volume support provided by the zone.

In addition, it will be seen that zone 11 is separated from zones 4 and 10. This is because in one embodiment, it is undesirable for fluid to flow from zone 4 or zone 10 into zone 11, since zone 11 corresponds to a location which will desire precise volume control.

Moreover, as shown in FIG. 15, zones 3, 6 and 7 are preferably smaller than zones 2, 5 and 8. This is because zones 3, 6 and 7 are provided near the base of the residual limb. The limb in these locations applies greater pressure to the zones 3, 6 and 7 than the limb in higher locations (e.g., zones 2, 5 and 8). Therefore, it is desired to control fluid more precisely in these zones.

The pressure applied to particular zones can also be adjusted using clinical data instructing how desired pressure can be applied to different portions of the residual limb to optimize blood flow. For example, temperature gradient studies or Doppler studies can be used to determine how much pressure may be desired to get blood flowing at a desired rate in particular locations of a residual limb. Using this information, the pressure within particular zones can be adjusted to optimize blood flow.

Thus, it will be appreciated that the zones can be advantageously arranged to provide desired control over migration of fluid depending on the amputee's needs. Zones can preferentially be opened to fluid to provide volume support in desired locations, for example, in an upper portion of the socket. At the same time, other zones can preferentially be closed to fluid to prevent fluid from migrating to locations where less volume support is needed, for example, in a lower portion of the socket. Furthermore, as described with respect to FIG. 15 above, differing pressure can be provided to different zones depending on particular muscles or blood accumulation.

The construction of the bladder system according to another embodiment is shown in FIGS. 17-20. FIGS. 17-20 shows different embodiments of cells having different shapes. Cells 1700, 1800, 1900, and 2000 all have similar functions; however, each cell 1700, 1800, 1900, and 2000 has a slightly different shape, and thus provides a slightly different feel for the amputee. Walls 1702, 1802, 1902, and 2002 represent the interior surface of the insert, which is in contact with liner 218 (FIG. 2C), while walls 1704, 1804, 1904, and 2004 represent the exterior surface of the insert, which is in contact with the socket 200 (FIG. 2A). Although the embodiments of FIGS. 17-20 do not show fluid ducts interconnecting adjacent cells, it will be appreciated that such fluid ducts can be provided. The cells can preferably be made using vacuum forming techniques or other techniques as described above. Preferably, the cells are manufactured so that they are as close together as possible, yet do not bump into one another when filled with fluid.

Figure 21:
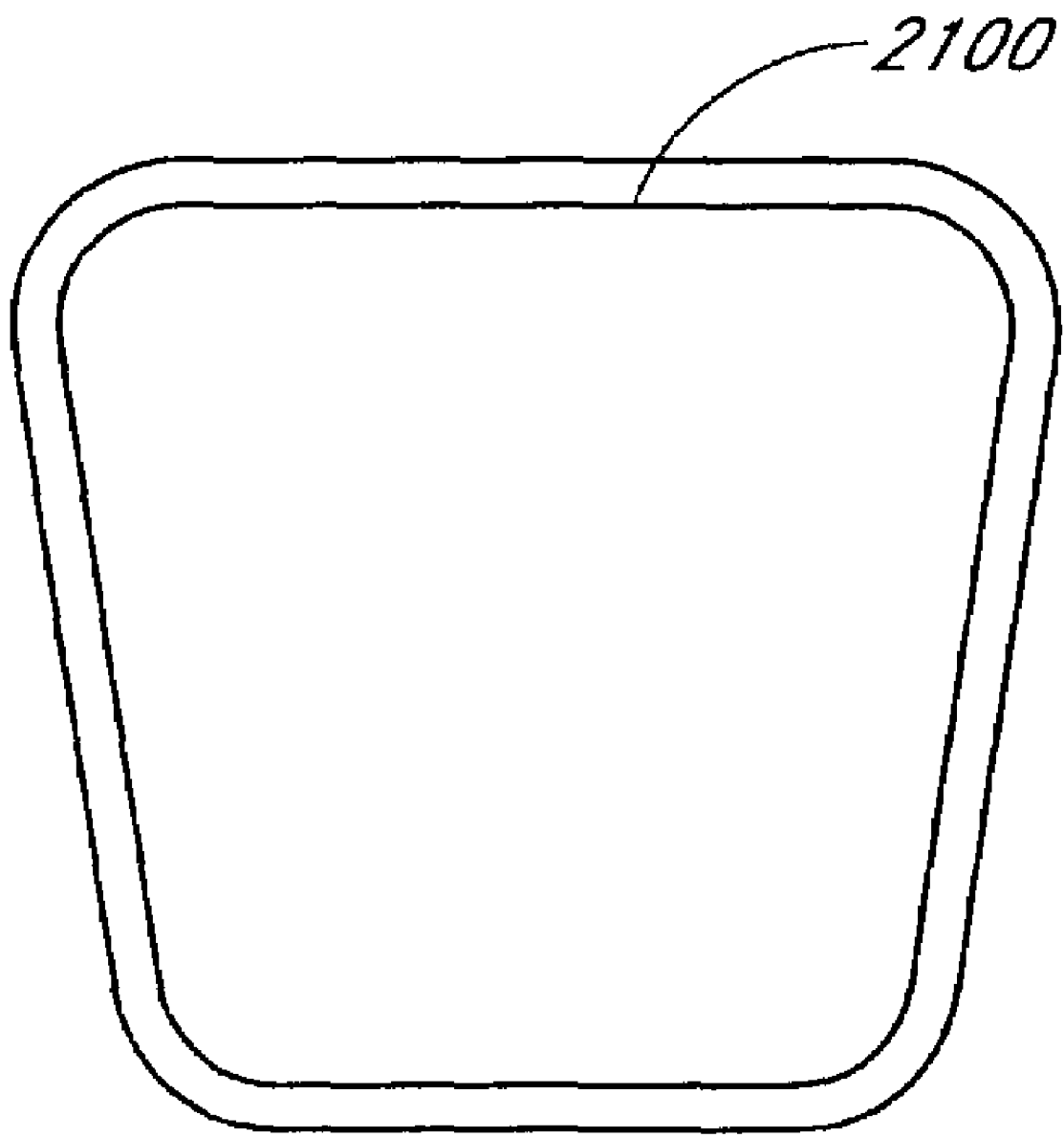
FIG. 21 is a cross-sectional view of another construction of the bladders of the socket insert of FIGS. 2A-C.

As shown in FIG. 21, one preferred embodiment utilizes polygonal shaped cells 2100, such as trapezoidal, rectangular or square. Other shapes may also be used, which provide the desired characteristics and handling. In a preferred embodiment, the cells are preferably about 0.75-1 in. in length and width, and about 0.2-0.25 in. thick, and more preferably 0.2 in. thick. The corners of the cells may also be curved for improved fluid flow.

In one embodiment, the fluid is moved between a reservoir and the cell array by the use of a peristaltic pump 2200 such as that shown in FIG. 22. As will be recognized by those skilled in the art, a peristaltic pump 2200 will generally comprise a section of tubing 2202 disposed between a housing and a peristaltic wheel 2224. A peristaltic wheel 2224 generally comprises a plurality of (six in the embodiment shown) protrusions 2210 or rollers rotatable about a central axis 2212. The protrusions 2210 are adapted to engage the tubing section 2202 disposed within the housing such that as the wheel 2224 is rotated, the tube is selectively compressed in a direction of desired fluid movement. The peristaltic wheel 2224 may alternatively comprise a variety of shapes, such as triangular, quadrilateral, octagonal, etc., as will be clear to those skilled in the art. The wheel is preferably driven by a stepper motor which is controlled by the controller. Thus, the peristaltic pump 2200 has the advantage that it may be controlled to provide bi-directional fluid motion toward 2206 or away from 2208 the cell array. Any pump known in the art may be used in accordance with the preferred embodiments of the present invention.

Figure 23:
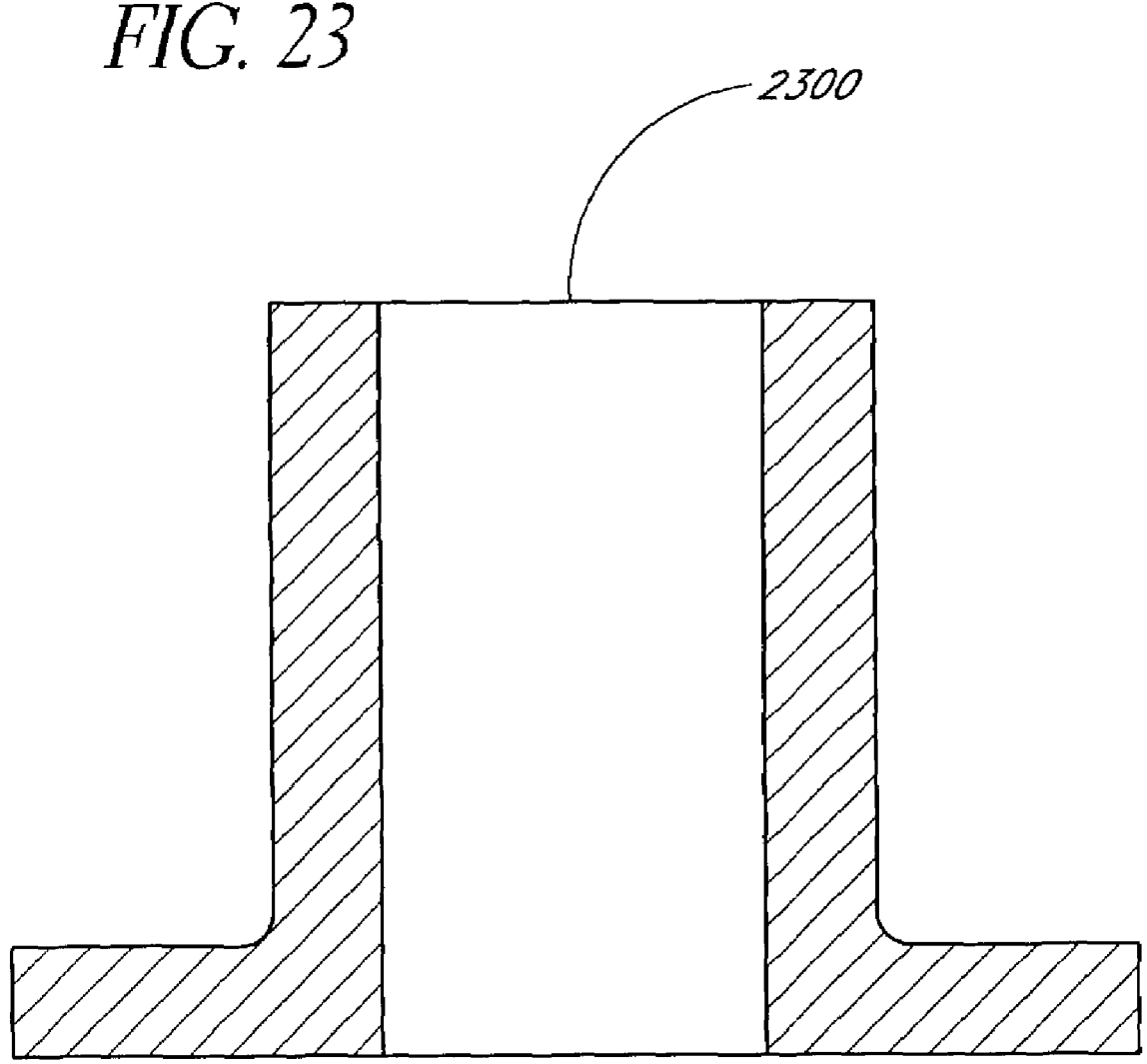
FIG. 23 is a detailed cross-sectional view of a tube seal flange for the socket insert of FIGS. 2A-C.
Figure 24B:
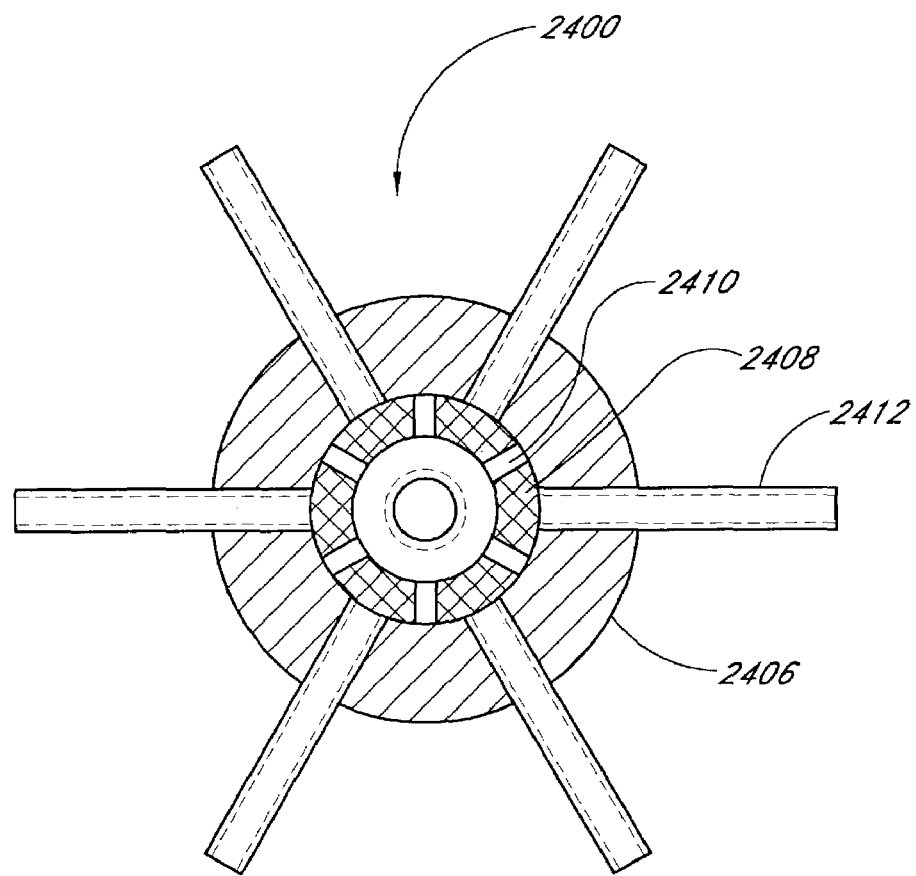
FIGS. 24A and 24B are a side view and cross-sectional view, respectively, of a central valve for the socket insert of FIGS. 2A-C.
Figure 24A:
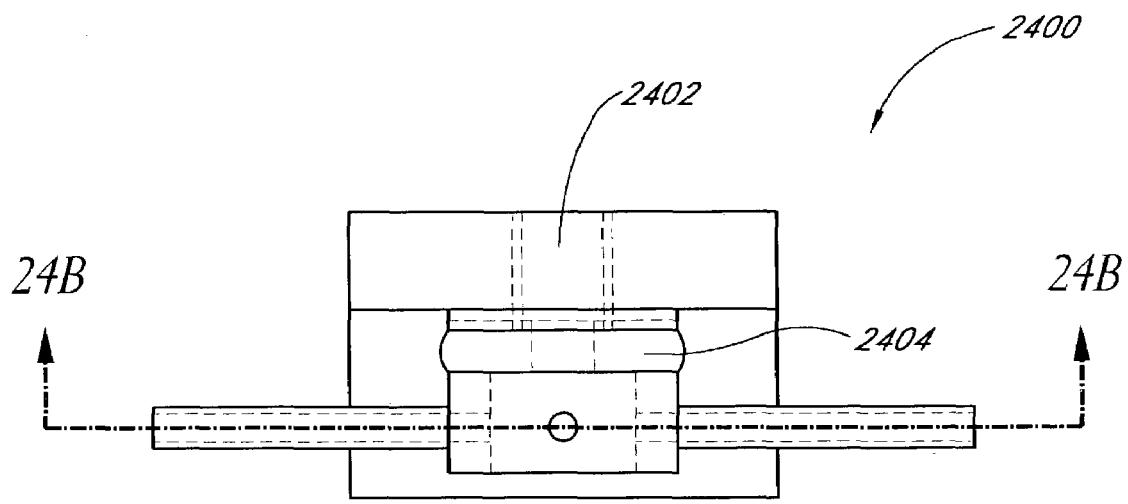

FIGS. 23-28B show different embodiments of valves for the bladder system of the preferred embodiments. FIG. 23 shows a detailed cross-sectional view of a tube seal flange 2300. Tube seal flange 2300 is preferably made of polyurethane. Such a tube can preferably have one side which is larger than the other side, such that fluid is slowed down in one direction but sped up in the other. Such a valve can be used between bladders or cells as described above, or between adjacent zones.

It will be appreciated that the fluid valves for use between adjacent cells or zones may also be gradually opened wider at one end than at the other. Depending on the parameters of the fluid valves, the fluid cell, and the pressure desired, it may be desirable to leave the fluid valves in a partially opened state permanently (a restriction) or it may be necessary to open fluid valves fully to allow fluid to reenter the fluid cells. Furthermore, each fluid valve may be replaced with a variable restriction.

In other embodiments, the fluid valves may be mechanically controlled or be manually adjustable pressure sensitive bleed valves. As the pressure reaches an adjusted threshold, the bleed valve opens until the pressure is below the threshold. Fluid may freely flow in through the bleed valve. A separate fluid duct, with a one way valve disposed therein, may also be provided to allow fluid to enter the fluid cells. In certain preferred embodiments, the valves are solenoid valves.

The size of the opening at the fluid valve should allow fluid to escape the fluid cell in a controlled manner. The fluid should not escape from the fluid cell so quickly that the fluid cell becomes fully deflated before the peak of the pressure exerted by the user. However, the fluid must be allowed to escape from the fluid cell at a high enough rate to provide the desired pressure. Factors which will bear on the size of the opening of the flow regulator include the viscosity of the fluid, the size of the fluid cell, the pressure exerted by fluid in the fluid reservoir, the peak pressure exerted and the length of time such pressure is exerted.

FIGS. 24-28 illustrate different embodiments for central valving that can be used to regulate flow between a central reservoir and individual bladders or zones of bladders (see, e.g., valve manifold 312 of FIG. 3). FIG. 24A shows a side view of a multiport valve 2400. Valve 2400 comprises a fill port 2402 and a snap fit rib seal 2404. FIG. 24B shows a cross-sectional view of multiport valve 2400. Valve 2400 preferably comprises a stationary housing 2406, made of polycarbonate. Valve 2400 also comprises a rotating valve bore 2408, shown in a closed position. When in an open position, fluid passageways 2410 permit fluid flow between hypodermic tubes 2412. Hypodermic tubes 2412 are in fluid communication with individual cells, zones, or a fluid reservoir. Thus, fluid pumped from a fluid reservoir can be directed through the valve 2400 to one or more zones or individual bladders as described above.

Figure 25B:
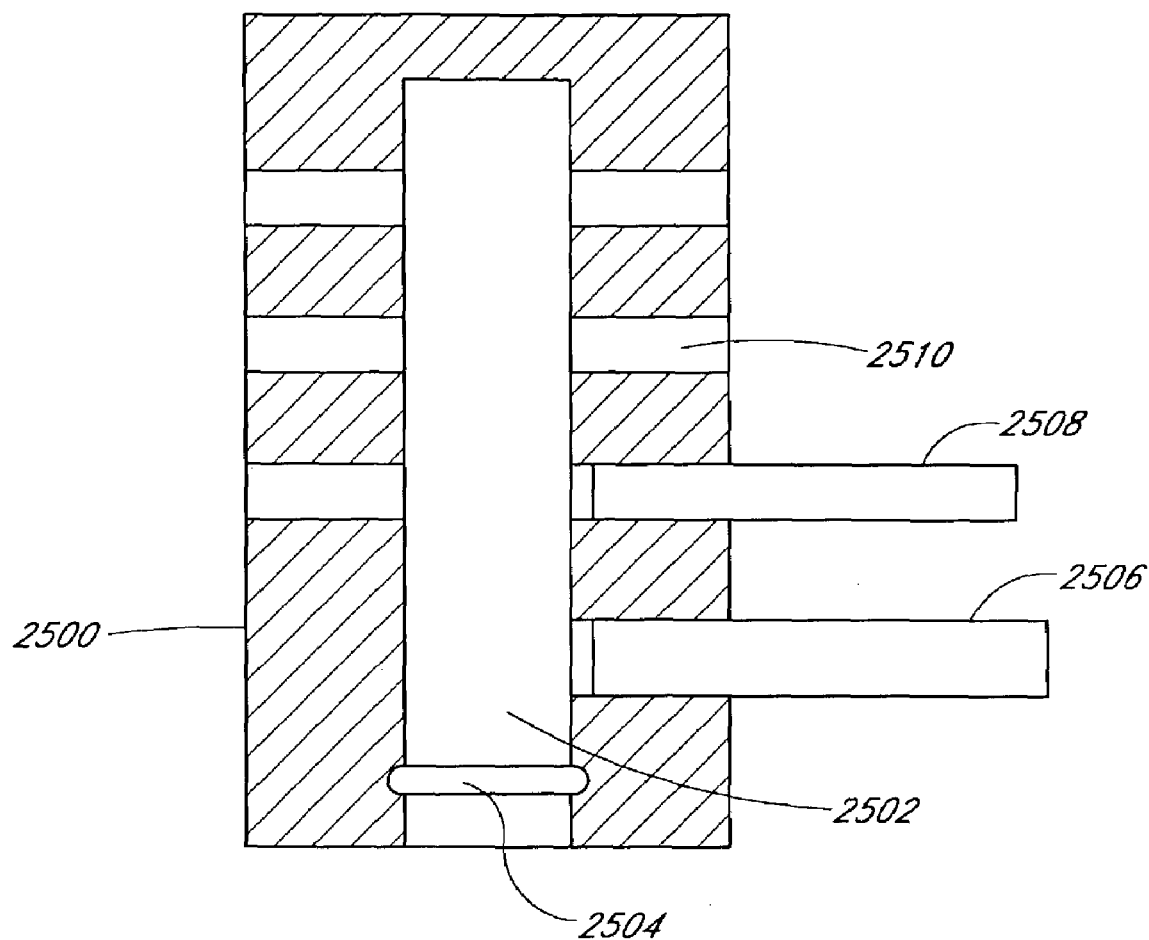
FIGS. 25A and 25B are an end view and cross-sectional view, respectively, of a central valve for the socket insert of FIGS. 2A-C.
Figure 25A:
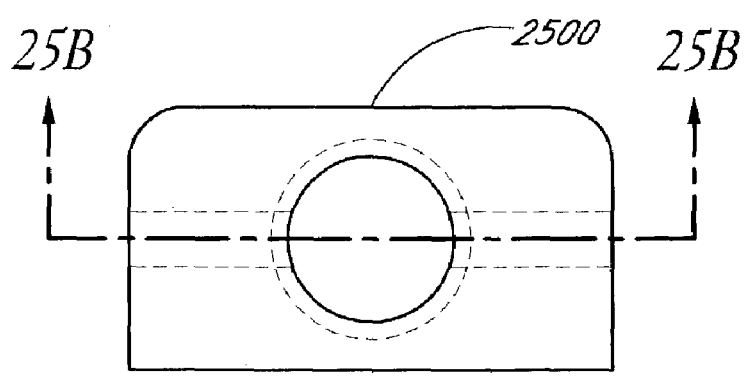

FIGS. 25A and 25B show an alternative embodiment of a valve used with the bladder system as described above. FIG. 25A shows a side view of valve 2500. FIG. 25B shows a cross-sectional view of valve 2500. Valve 2500 comprises a central passageway 2502. A stop 2504 may be provided to prevent fluid leakage through passageway 2502. Different sized passageways 2506, 2508, 2510 are in fluid communication with individual cells, zones, or a fluid reservoir.

Figure 26B:
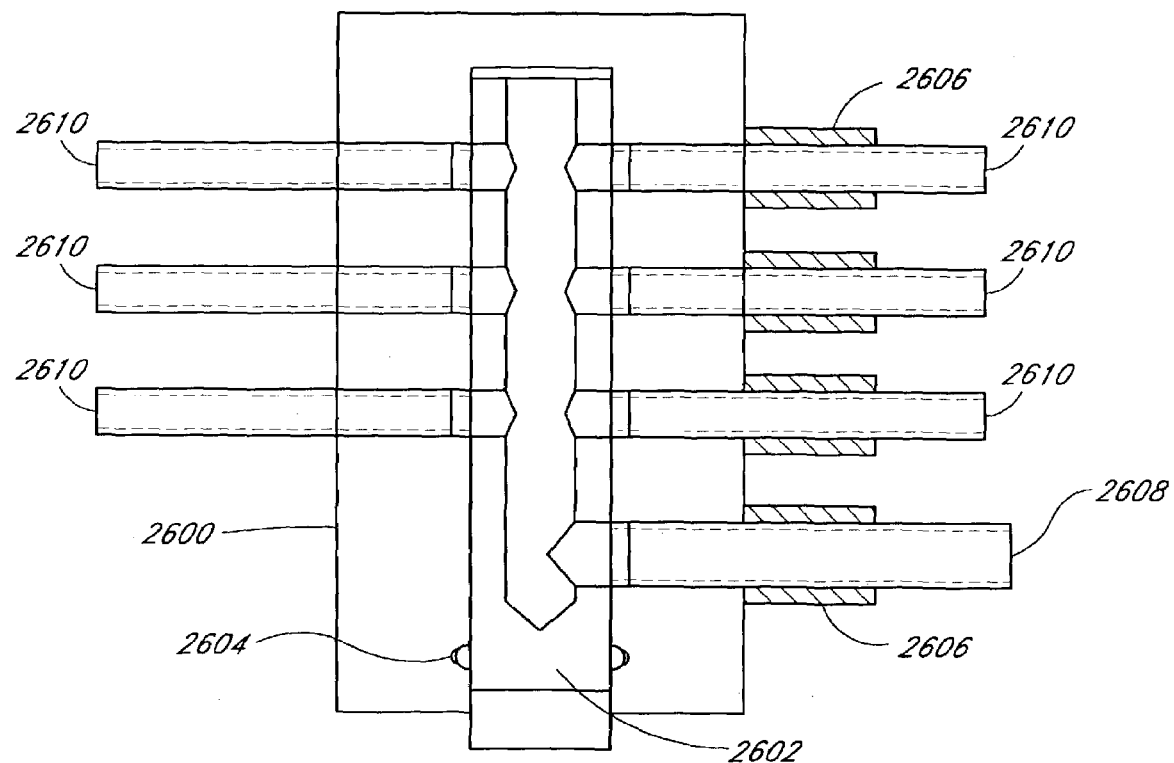
FIGS. 26A and 26B are an end view and cross-sectional view, respectively, of a central valve for the socket insert of FIGS. 2A-C.
Figure 26A:
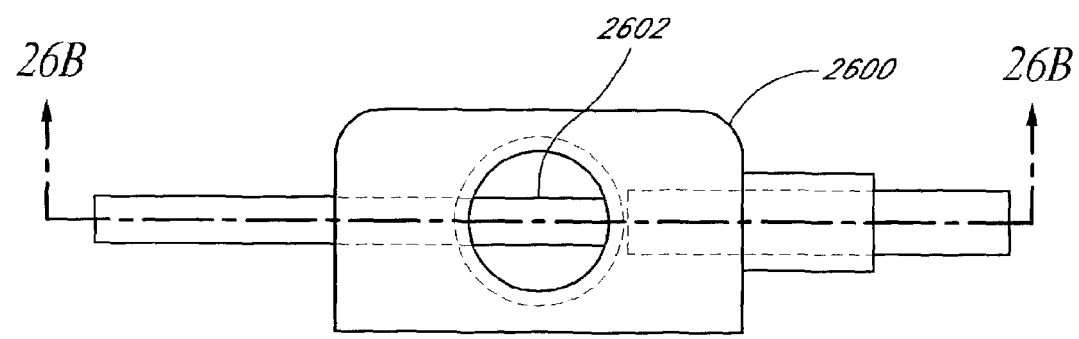

FIGS. 26A and 26B show a microbore tube valve 2600 of an embodiment used with the bladder system as described above. FIG. 26A shows an end view of valve 2600. FIG. 26B shows a cross-sectional view of valve 2600. Valve 2600 preferably comprises a rotary inner core 2602. Valve 2600 also includes a snap seal 2604. Flexible microbore tubing 2606 is press fit into valve 2600, for receiving hypotubes 2608, 2610. Tubing 2608, 2610 is in fluid communication with individual cells, zones, or a reservoir, depending on the particular embodiment.

Figure 27B:
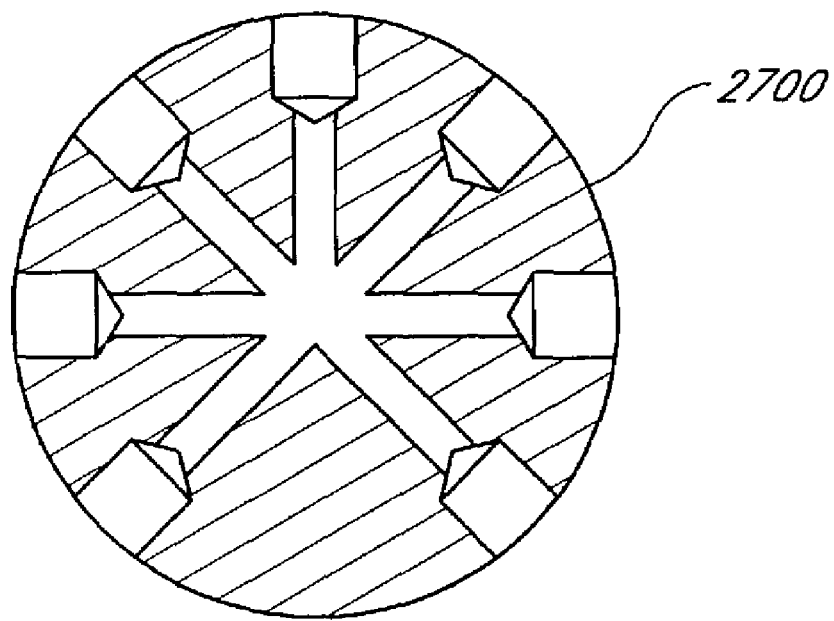
FIGS. 27A and 27B are cross-sectional views of a tube connector for the socket insert of FIGS. 2A-C.
Figure 27A:
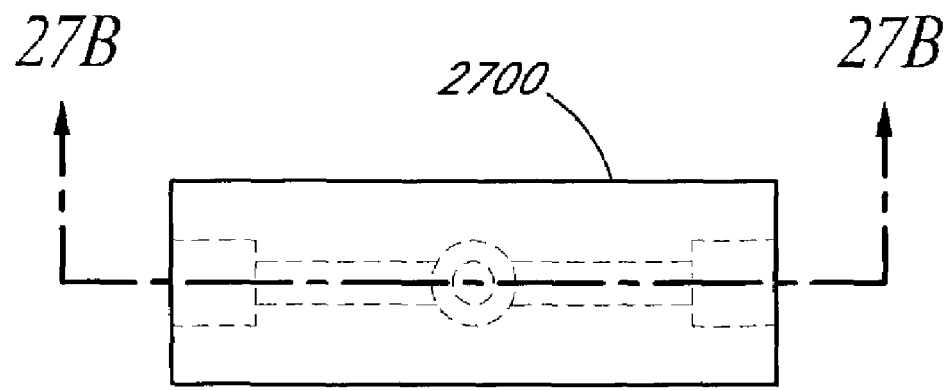

FIGS. 27A and 27B show a tube connector 2700, for receiving and distributing fluid to appropriate zones or cells. FIG. 27A shows a side cross-sectional view of connector 2700. FIG. 27B shows a top cross-sectional view of connector 2700. Connector 2700 is a multiport valve manifold.

Figure 28B:
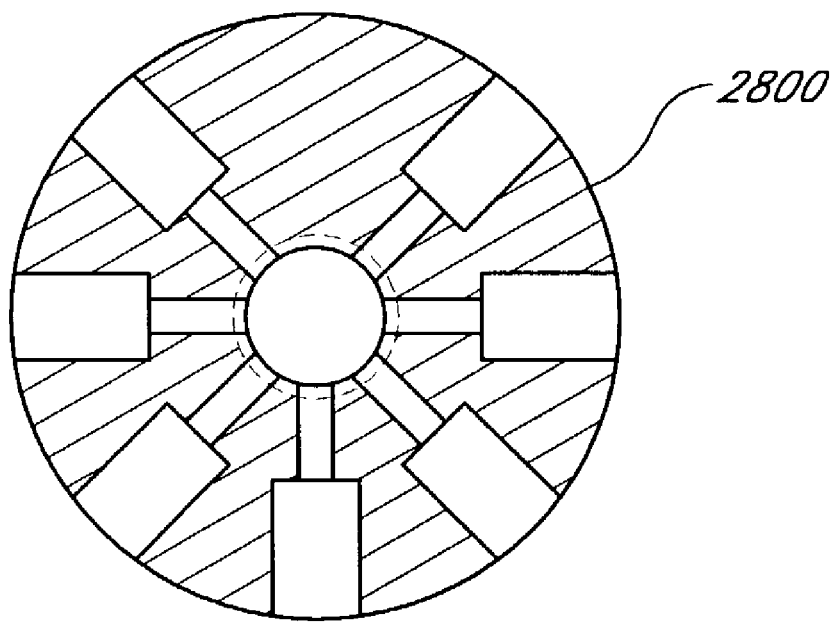
FIGS. 28A and 28B are cross-sectional views of a tube connector for the socket insert of FIGS. 2A-C.
Figure 28A:
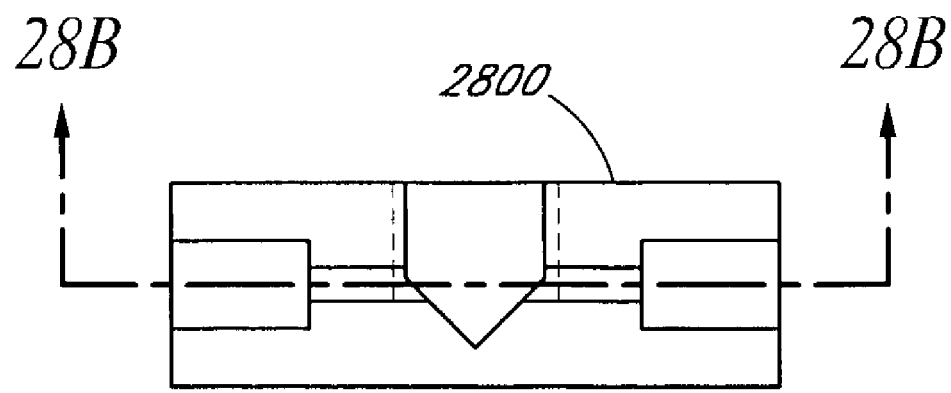

FIGS. 28A and 28B show an alternative embodiment of a tube connector 2800. FIG. 28A shows a side cross-sectional view of connector 2800. FIG. 28B shows a top cross-sectional view of connector 2800. Connector 2800 is a multiport valve manifold.

The methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

The foregoing description with attached drawings is only illustrative of possible embodiments of the described method and should only be construed as such. Other persons of ordinary skill in the art will realize that many other specific embodiments are possible that fall within the scope and spirit of the present idea. The scope of the invention is indicated by the following claims rather than by the foregoing description. Any and all modifications which come within the meaning and range of equivalency of the following claims are to be considered within their scope.

What is claimed is:

1. A prosthetic device, comprising:
a socket, said socket sized and configured for receiving a residual limb, said socket including a plurality of bladders being adapted to receive a fluid medium, wherein said bladders are organized into a plurality of zones, each of said zones including a plurality of bladders in fluid communication with one another within said zone, at least one of said plurality of zones being in fluid communication with at least one other zone, said fluid communication between said at least two zones being more limited than the fluid communication among bladders within a given zone, further comprising a fluid medium within said bladders, wherein the fluid medium is incompressible.

2. The device of claim 1, wherein each of the bladders has a maximum dimension of about 2 inches or less.

3. The device of claim 1, wherein the zones are arranged to correspond to different muscle groups of the residual limb.

4. The device of claim 1, wherein at least some of the zones have differing number of bladders, zones having a small number of bladders being arranged to correspond to locations of the residual limb experiencing greater volume fluctuations.

5. The device of claim 1, wherein the bladders are organized into at least four zones.

6. The device of claim 5, wherein each of the zones includes at least four interconnected bladders.

7. The device of claim 1, comprising eight or more zones.

8. The device of claim 1, wherein the device is wing-shaped.

9. The device of claim 1, further comprising: a pump to control fluid flow into and/or out of said zones.

10. The device of claim 9, in which said pump and said zones are adapted so that different zones can be filled with fluid at differing pressures.

11. The device of claim 1, further comprising a pump adapted to control fluid flow into and/or out of said bladders.

12. The device of claim 11, in which said pump and said bladders are adapted so that different bladders can be filled with fluid at differing pressures.

13. A prosthetic device, comprising:
a socket for receiving a residual limb, the socket having an interior surface; and
a plurality of bladders in fluid communication with an incompressible fluid medium positioned at least partially on the interior surface, wherein said bladders are organized into a plurality of zones, each of said zones including a plurality of bladders and wherein each of the bladders within a zone are in fluid communication with the other bladders within said zone, wherein each of said zones includes at least four interconnected bladders, at least one of said plurality of zones being in fluid communication with at least one other zone, said fluid communication between said at least two zones being more limited than the fluid communication among bladders within a given zone.

14. A prosthetic device, comprising:
a socket for receiving a residual limb, the socket having an interior surface; and
a plurality of bladders being adapted to receive an incompressible fluid medium positioned at least partially on the interior surface, wherein said bladders are organized into a plurality of zones, each of said zones including a plurality of bladders and wherein each of the bladders within a zone are in fluid communication with the others bladders within said zone, wherein each of said zones includes at least four interconnected bladders, at least one of said plurality of zones being in fluid communication with at least one other zone, said fluid communication between said at least two zones being more limited than the fluid communication among bladders within a given zone;
wherein the plurality of bladders are positioned only partially circumferentially around the interior surface of the socket; and
further comprising a fluid medium within said bladders, wherein the fluid medium is incompressible.

15. The prosthetic device of claim 13 or claim 14, wherein the bladders are organized into at least four zones.

16. The prosthetic device of claim 13 or claim 14, wherein each of the bladders has a maximum dimension of about 2 inches or less.

17. A prosthetic device, comprising:
a socket for receiving a residual limb, the socket having an interior surface; and
a plurality of bladders being adapted to receive an incompressible fluid medium positioned at least partially on the interior surface, wherein said bladders are organized into a plurality of zones, each of said zones including a plurality of bladders and wherein each of the bladders within a zone are in fluid communication with the other bladders within said zone, at least one of said plurality of zones being in fluid communication with at least one other zone, said fluid communication between said at least two zones being more limited than the fluid communication among bladders within a given zone;
wherein the zones are arranged to correspond to different muscle groups of the residual limb; and
further comprising a fluid medium within said bladders, wherein the fluid medium is incompressible.

18. A prosthetic device, comprising:
a socket; and
a plurality of bladders in fluid communication with an incompressible fluid, and sized and configured to be positioned adjacent an interior surface of said socket, wherein each of said bladders has a maximum dimension of about 2 inches or less, and wherein at least some of the bladders are organized into interconnected zones, each zone having a plurality of bladders interconnected such that fluid can flow from one bladder to another bladder within said zone, and wherein each zone includes at least four bladders, said fluid communication between at least two zones being more limited than the fluid communication among bladders within a given zone, and wherein flow into and out of said zones is controllable such that different zones can be filled with fluid to differing pressures.

19. The prosthetic device of claim 18, wherein said socket is configured to receive said plurality of bladders.

20. The prosthetic device of claim 18, wherein the plurality of bladders are provided on a socket insert.

21. The prosthetic device of claim 20, wherein the socket insert is secured to an interior surface of a socket.

22. The prosthetic device of claim 21, wherein the socket insert is provided only along a posterior portion of the interior surface of the socket.

23. The prosthetic device of claim 18, wherein the plurality of bladders is organized into at least four zones.

24. The prosthetic device of claim 18, wherein the plurality of bladders is organized into at least eight zones.

25. The prosthetic device of claim 18, wherein each of the bladders within a zone are interconnected.

26. The prosthetic device of claim 18, further comprising:
an on-board automatic pump to control fluid flow into and out of said zones such that different zones can be filled with fluid to differing pressures.

27. A prosthetic device, comprising:
a socket;
a plurality of bladders sized and configured to be positioned adjacent an interior surface of said socket, at least some of the bladders containing an incompressible fluid, wherein each of said bladders has a maximum dimension of about 2 inches or less, wherein at least some of the bladders are interconnected in a web-like configuration and not in a line-like series connected end-to-end, and an on-board pump energized by an energy source other than the user controls-fluid flow from one bladder to another.

28. A prosthetic device, comprising:
a socket; and
a socket insert for insertion into the socket, said socket insert sized or configured for receiving a residual limb, said socket insert including a plurality of bladders being adapted to receive a fluid medium, wherein said bladders are organized into a plurality of zones, each of said zones including a plurality of bladders in fluid communication with one another within said zone, at least one of said plurality of zones being in fluid communication with at least one other zone, said fluid communication between said at least two zones being more limited than the fluid communication among bladders within a given zone, further comprising a fluid medium within said bladders, wherein the fluid medium is incompressible.

29. The device of claim 28, wherein each of the bladders has a maximum dimension of about 2 inches or less.

30. The device of claim 28, wherein the zones are arranged to correspond to different muscle groups of the residual limb.

31. The device of claim 28, wherein at least some of the zones have differing number of bladders, zones having a small number of bladders being arranged to correspond to locations of the residual limb experiencing greater volume fluctuations.

32. The device of claim 28, wherein the bladders are organized into at least four zones.

33. The device of claim 32, wherein each of the zones includes at least four interconnected bladders.

34. The device of claim 28, comprising eight or more zones.

35. The device of claim 28, wherein the insert is wing-shaped.

36. A prosthetic device, comprising:
a socket having an interior surface;
a socket insert for insertion into the socket, said socket insert sized or configured for receiving a residual limb; and a plurality of bladders in fluid communication with an incompressible fluid medium, said bladders supported at least partially by the socket's interior surface, wherein said bladders are organized into a plurality of zones, each of said zones including a plurality of bladders and wherein each of the bladders within a zone are in fluid communication with the other bladders within said zone, at least one of said plurality of zones being in fluid communication with at least one other zone, said fluid communication between said at least two zones being more limited than the fluid communication among bladders within a given zone.

37. A prosthetic device, comprising:
a socket insert for insertion into a socket that has an interior surface, said socket insert sized or configured for receiving a residual limb; and
a plurality of bladders being adapted to receive an incompressible fluid medium, at least some of the bladders adapted to be positioned to at least partially contact and be supported by an interior surface of the socket, wherein said bladders are organized into a plurality of zones, each of said zones including a plurality of bladders and wherein each of the bladders within a zone are in fluid communication with the other bladders within said zone, at least one of said plurality of zones being in fluid communication with at least one other zone, said fluid communication between said at least two zones being more limited than the fluid communication among bladders within a given zone;
wherein the plurality of bladders are positioned only partially circumferentially around an interior surface of the socket; and
further comprising a fluid medium within said bladders, wherein the fluid medium is incompressible.

38. The device of claim 1 or claim 50 or claim 36 or claim 37, wherein each of the bladders has a maximum dimension of about 1 inch or less.

39. The prosthetic device of claim 36 or claim 37, wherein the bladders are organized into at least four zones.

40. The prosthetic device of claim 36 or claim 37, wherein each of the zones includes at least four interconnected bladders.

41. The prosthetic device of claim 36 or claim 37, wherein each of the bladders has a maximum dimension of about 2 inches or less.

42. The prosthetic device of claim 36 or claim 37, wherein the zones are arranged to correspond to different muscle groups of the residual limb.

43. The prosthetic device of claim 1 or 28 or 37, further comprising:
a means to limit the compression of at least one of the plurality of bladders sufficiently to prevent the bladder from bottoming out during anticipated loading by the residual limb.

44. A prosthetic device, comprising:
a socket insert for insertion into a socket, said socket configured for receiving a residual limb;
a plurality of bladders in fluid communication with an incompressible fluid, at least some of the bladders having generally vertical side walls abutting adjacent bladders; and
a fluid manifold associated with the socket insert and the plurality of bladders, said manifold sized and configured and connected to the bladders to permit and allow control of the flow of the incompressible fluid among and within the bladders.

45. The prosthetic device of claim 44, further comprising:
a fluid reservoir;
wherein said bladders are organized into a plurality of zones, each of said zones including at least two bladders in fluid communication with each other, said zones also in fluid communication with each other via the fluid manifold.

46. The prosthetic device of claim 45, wherein at least one sensor is positioned on a bottom of a socket.

47. The prosthetic device of claim 45, wherein the zones are positioned on substantially all of the socket insert.

48. The prosthetic device of claim 45, said manifold including means for manual actuation of fluid flow between zones.

49. The prosthetic device of claim 45, said manifold including control means for preventing undesired migration of fluid among the bladders and/or zones.

50. The prosthetic device of claim 45, further including at least one pressure sensor associated with the socket insert to assist in controlling the location of fluid within the socket insert.

51. The prosthetic device of claim 50, wherein the pressure sensor is positioned within a duct connecting zones.

52. The prosthetic device of claim 50, further including a central processing unit responsive to input from the at least one pressure sensor.

53. The prosthetic device of claim 44, wherein the bladders are sized and configured and located and fabricated from material so that, during normal use, adjacent bladders are in direct lateral contact with each other and provide substantial uninterrupted support for the residual limb without substantial unsupported areas between adjacent bladders.

54. The prosthetic device of claim 44, further including at least one pressure sensor associated with the socket insert to assist in controlling the location of fluid within the socket insert.

55. The prosthetic device of claim 44, said manifold including control means for preventing undesired migration of fluid among the bladders.

56. A socket insert apparatus for insertion into a socket, said socket insert sized or configured for receiving a residual limb, the socket insert apparatus comprising:
a plurality of bladders in fluid communication with an incompressible fluid; and a fluid manifold associated with the socket insert and the plurality of bladders, said manifold sized and configured and connected to the bladders to permit and allow control of the flow of the incompressible fluid among and within the bladders;
the socket insert apparatus further comprising:
a fluid reservoir;
wherein said bladders are organized into a plurality of zones, each of said zones including at least two bladders in fluid communication with each other, said zones also in fluid communication with each other via the fluid manifold, said fluid communication between said zones being more limited than the fluid communication among bladders within a given zone; and wherein the socket insert includes snaps for mounting the insert inside the socket.

57. A prosthetic device, comprising:
a plurality of bladders adapted to receive a selected small volume of an incompressible fluid, said bladders sized and configured to be positioned generally in a layer between an interior surface of a socket and a residual limb inserted into the socket, said bladders being not larger than 1 inch by 1 inch and forming a generally rectangular bladder, and wherein at least some of the bladders are organized into interconnected zones, each zone having a plurality of bladders interconnected such that fluid can flow from one bladder to another bladder within said zone, said fluid communication between at least two zones being more limited than the fluid communication among bladders within a given zone;

wherein the plurality of bladders are provided on a socket insert;

wherein the socket insert is provided only along a portion of an interior surface of a socket.

58. A socket having a plurality of bladders containing incompressible fluid, wherein at least two of the bladders each have generally vertical sidewall portions, said bladders arranged generally adjacent to each other over at least a portion of an interior surface of the socket and forming a substantially uninterrupted supporting surface for a residual limb placed into the socket, further including means to minimize motion of the residual limb with respect to the socket, said means including the bladders being sufficiently small to limit the amount of movement of the incompressible fluid contained within the bladders.

59. A socket having a plurality of bladders containing incompressible fluid, wherein at least one of the bladders has a generally vertical sidewall portion, said bladders arranged generally adjacent to each other over at least a portion of an interior surface of the socket and forming a substantially uninterrupted supporting surface for a residual limb placed into the socket, further including means to minimize motion of the residual limb with respect to the socket, said means including the bladders being sufficiently small to limit the amount of movement of the incompressible fluid contained within the bladders.

60. The socket of claim 58 or 59, further comprising:

at least one of the bladders being shaped to define a sidewall portion.

61. The socket of claim 58 or 59, further comprising:

at least some of the bladders having at least one corner when viewed in cross section.

62. The socket of claim 61, further comprising: said at least one corner being at least partially curved.

63. The socket of claim 58 or 59, further comprising:

at least one of the bladders includes an upper surface of the bladder and a lower surface of the bladder, and a sidewall portion extending between the upper and lower surfaces of the bladder, said sidewall portion spacing the upper and lower surfaces from each other.

* * * * *